US012685540B2

(12) United States Patent
Jaramaz et al.

(10) Patent No.: US 12,685,540 B2
(45) Date of Patent: Jul. 21, 2026

(54) SYSTEMS AND METHODS FOR NAVIGATED REAMING OF THE ACETABULUM

(71) Applicants: Smith & Nephew, Inc., Memphis, TN (US); Smith & Nephew Asia Pacific Pte. Limited, Singapore (SG); Smith & Nephew Orthopaedics AG, Zug (CH)

(72) Inventors: Branislav Jaramaz, Pittsburgh, PA (US); Rahul Khare, Sewickley, PA (US); Constantinos Nikou, Monroeville, PA (US); Samuel C. Dumpe, Sewickley, PA (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 0 days.

(21) Appl. No.: 18/876,470

(22) PCT Filed: Jun. 15, 2023

(86) PCT No.: PCT/US2023/025394
§ 371 (c)(1),
(2) Date: Dec. 18, 2024

(87) PCT Pub. No.: WO2023/249876
PCT Pub. Date: Dec. 28, 2023

(65) Prior Publication Data
US 2025/0302490 A1 Oct. 2, 2025

Related U.S. Application Data

(60) Provisional application No. 63/366,654, filed on Jun. 20, 2022.

(51) Int. Cl.
*A61B 17/16* (2006.01)
*A61B 34/10* (2016.01)
(Continued)

(52) U.S. Cl.
CPC ...... *A61B 17/1604* (2013.01); *A61B 17/1626* (2013.01); *A61B 17/1666* (2013.01);
(Continued)

(58) Field of Classification Search
CPC .... A61B 2034/2055; A61B 2034/2051; A61B 2034/107; A61B 2034/2063;
(Continued)

(56) References Cited

U.S. PATENT DOCUMENTS

2021/0192759 A1* 6/2021 Lang ...................... A61B 90/37

* cited by examiner

*Primary Examiner* — Samuel S Hanna
(74) *Attorney, Agent, or Firm* — KDW Firm PLLC

(57) ABSTRACT

Systems and methods for real-time navigation of reaming of an acetabulum are disclosed. A first tracking element is interfaced to a reamer. A second tracking element is interfaced at or near the acetabulum. The first tracking element can be interfaced to an outer casing surrounding a portion of the shaft of the reamer. A depth and a tilt angle of the reamer with respect to the acetabulum are determined, based on a location of the first and second tracking elements. Based on a surgical plan, the depth and the tilt angle, the volume of removed bone from the acetabulum can also be determined.

6 Claims, 9 Drawing Sheets

(51) Int. Cl.
*A61B 34/20*       (2016.01)
*G16H 40/63*       (2018.01)
*A61B 17/00*       (2006.01)

(52) U.S. Cl.
CPC .............. *A61B 34/10* (2016.02); *A61B 34/20*
              (2016.02); *G16H 40/63* (2018.01); *A61B
                2017/00022* (2013.01); *A61B 2034/102*
              (2016.02); *A61B 2034/105* (2016.02); *A61B
                2034/107* (2016.02); *A61B 2034/2055*
                                            (2016.02)

(58) Field of Classification Search
CPC ...... A61B 2034/2065; A61B 2090/062; A61B
              2090/067; A61B 34/20; A61B 34/10;
                                        A61B 17/1666
See application file for complete search history.

SYSTEMS AND METHODS FOR NAVIGATED REAMING OF THE ACETABULUM

RELATED APPLICATIONS

The present application is a U.S. national stage application from International Patent Application No. PCT/US2023/025394, titled SYSTEMS AND METHODS FOR NAVIGATED REAMING OF THE ACETABULUM, filed Jun. 15, 2023, which claims priority to U.S. Provisional Patent Application No. 63/366,654, titled SYSTEMS AND METHODS FOR NAVIGATED REAMING OF THE ACETABULUM, filed Jun. 20, 2022, which is hereby incorporated by reference herein in its entirety.

TECHNICAL FIELD

The present disclosure relates generally to methods, systems, and apparatuses related to a computer-assisted surgical system that includes various hardware and software components that work together to enhance surgical workflows. The disclosed techniques may be applied to, for example, hip arthroplasties.

BACKGROUND

Total hip arthroplasty (THA) is generally considered one of the most successful procedures in orthopedic surgery. However, despite this general reputation, a number of complications related to the procedure still exist, including aseptic loosening, early dislocation following THA, and misalignment. Some of these complications may be related to the surgical techniques deployed for THA and the ability of the surgeon to remain within the confines of a surgical plan.

Specifically, reaming of the acetabulum is an important step in THA that requires modelling and surgical planning. Even with adequate planning, the surgeon must employ a high degree of accuracy during reaming in order to successfully carry out the procedure according to the surgical plan.

In the past, computer-assisted surgical systems have approached reaming of the acetabulum in a directly volumetric sense. For example, the position of the tool and the bone may be tracked in 3D space and their relative positions may be monitored during reaming. The relative 3D positions may be interpreted to determine, on a bone model, the voxels of bone that are removed during reaming.

However, tracking and assessing individual voxels of bone is a complex process that requires a higher amount of computing resources in order to perform the monitoring in real time. Real-time calculation is important in order to guide the surgeon during the reaming procedure. Especially with a tool such as a reamer where the head is quite large, voxel-by-voxel assessment may be overly complex and may complicate the real-time monitoring process.

Furthermore, volumetric tracking requires a high degree of accuracy to be performed satisfactorily, i.e., on the scale of individual voxels. This is particularly true during a procedure such as reaming where a relatively low volume of bone is being removed.

Surgeons would benefit greatly from real-time guidance and/or navigation tools that determine the pathway of the reamer to assess compliance with a surgical plan. Furthermore, safety features that prevent reaming beyond a threshold margin of the surgical plan would prevent post-operative complications and increase overall success and satisfaction rates for THA procedures.

SUMMARY

In some embodiments, a method of performing navigated reaming of an acetabulum includes receiving a surgical plan. The surgical plan can include one or more patient-specific parameters associated with a total hip arthroplasty. The parameters can further include a planned implant location and orientation. The method of performing navigated reaming of an acetabulum further includes receiving a three-dimensional model of at least a portion of the acetabulum, providing a first tracking element associated with a reamer, providing a second tracking element associated with the acetabulum, receiving information associated with a geometry of the reamer, determining at least one of a depth and a tilt angle of the reamer with respect to the acetabulum and the planned implant location and orientation, based on a location of the first tracking element, a location of the second tracking element, and the information associated with the geometry of the reamer, and modifying the three-dimensional model based on at least one of the depth and the tilt angle.

In some embodiments, the method further includes comparing the tilt angle with a threshold range of angles; and responsive to the tilt angle lying outside the threshold range of angle, automatically deactivating or reducing the speed of the reamer.

In some embodiments, the method further includes comparing the depth with a threshold depth; and responsive to the depth exceeding the threshold depth, automatically deactivating or reducing the speed of the reamer.

In some embodiments, the method further includes receiving a size of a reamer head.

In some embodiments, the method further includes generating a three-dimensional model of the reamer head; and displaying, on a display device, the three-dimensional model of the reamer head relative to the three-dimensional model of at least a portion of the acetabulum.

In some embodiments, the method further includes generating an updated three-dimensional model of at least a portion of the acetabulum, based on the three-dimensional model of at least a portion of the acetabulum, and at least one of the depth and the tilt angle.

In some embodiments, the surgical plan includes a three-dimensional model of one or more planned modifications to the acetabulum, the method further including: comparing the updated three-dimensional model of at least a portion of the acetabulum and the three-dimensional model of the one or more planned modifications to the acetabulum; and displaying indicia on the updated three-dimensional model of at least a portion of the acetabulum based on the comparison.

In some embodiments, receiving information associated with the geometry of the reamer further includes providing a third tracking element configured to interface to the reamer in-place of a reamer head; and determining the information associated with the geometry of the reamer based on the location of the first tracking element with respect to a location of the third tracking element.

In some embodiments, providing a first tracking element associated with the reamer further includes interfacing the first tracking element to an outer casing of the reamer, wherein the outer casing surrounds a portion of a shaft of the reamer, wherein the shaft is configured to rotate with respect to the outer casing.

In some embodiments, the reamer is supported using a passive arm.

In some embodiments, the first tracking element is affixed to the passive arm.

In some embodiments, a method of performing navigated reaming of an acetabulum includes receiving a surgical plan. The surgical plan can include one or more patient-specific parameters associated with a total hip arthroplasty. The parameters can further include a planned implant location and orientation. The method further includes providing a first tracking element associated with a reamer, providing a second tracking element registered with respect to the planned implant location and orientation; receiving information associated with a geometry of the reamer, and determining at least one of a depth and a tilt angle of the tool with respect to the planned implant location and orientation, based on a location of the first tracking element, a location of the second tracking element, and the information associated with the geometry of the reamer.

In some embodiments, a system for performing navigated reaming of an acetabulum includes a navigational tracking system, a reamer, a first tracking element, affixed to the reamer and configured to be tracked by the navigational tracking system, a second tracking element, affixed to an acetabulum and configured to be tracked by the navigational tracking system, and a processor in communication with the navigational tracking system. The processor can be configured to receive a surgical plan, wherein the surgical plan includes one or more patient-specific parameters associated with a total hip arthroplasty, and wherein the parameters further include a planned implant location and orientation, receive a three-dimensional model of at least a portion of the acetabulum, determine at least one of a depth and a tilt angle of the reamer with respect to the acetabulum and the planned implant location and orientation, based on a location of the first tracking element, a location of the second tracking element, and the information associated with the geometry of the reamer, and modify the three-dimensional model based on at least one of the depth and the tilt angle.

In some embodiments, the processor is further configured to compare the tilt angle with a threshold range of angles; and responsive to the tilt angle lying outside the threshold range of angle, automatically deactivate or reduce the speed of the reamer.

In some embodiments, the processor is further configured to compare the depth with a threshold depth; and responsive to the depth exceeding the threshold depth, automatically deactivate or reduce the speed of the reamer.

In some embodiments, the processor is further configured to receive a size of a reamer head.

In some embodiments, the system further includes a display device. The processor can be further configured to generate a three-dimensional model of the reamer head; and display, on the display device, the three-dimensional model of the reamer head relative to the three-dimensional model of at least a portion of the acetabulum.

In some embodiments, the processor is further configured to generate an updated three-dimensional model of at least a portion of the acetabulum, based on the three-dimensional model of at least a portion of the acetabulum, and at least one of the depth and the tilt angle.

In some embodiments, the surgical plan includes a three-dimensional model of one or more planned modifications to the acetabulum; and wherein the processor is further configured to: compare the updated three-dimensional model of at least a portion of the acetabulum and the three-dimensional model of the one or more planned modifications to the acetabulum; and display indicia on the updated three-dimensional model of at least a portion of the acetabulum based on the comparison.

In some embodiments, the system further includes a third tracking element configured to interface to the reamer in-place of a reamer head. The processor can be further configured to determine the information associated with the geometry of the reamer based on the location of the first tracking element with respect to a location of the third tracking element.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings.

DETAILED DESCRIPTION

This disclosure is not limited to the particular systems, devices and methods described, as these may vary. The terminology used in the description is for the purpose of describing the particular versions or embodiments only and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Definitions

For the purposes of this disclosure, the term "implant" is used to refer to a prosthetic device or structure manufactured to replace or enhance a biological structure. For example, in a total hip replacement procedure a prosthetic acetabular cup (implant) is used to replace or enhance a patients worn or damaged acetabulum. While the term "implant" is generally considered to denote a man-made structure (as contrasted with a transplant), for the purposes of this specification an implant can include a biological tissue or material transplanted to replace or enhance a biological structure.

For the purposes of this disclosure, the term "real-time" is used to refer to calculations or operations performed on-the-fly as events occur or input is received by the operable system. However, the use of the term "real-time" is not intended to preclude operations that cause some latency between input and response, so long as the latency is an unintended consequence induced by the performance characteristics of the machine.

Although much of this disclosure refers to surgeons or other medical professionals by specific job title or role, nothing in this disclosure is intended to be limited to a specific job title or function. Surgeons or medical professionals can include any doctor, nurse, medical professional, or technician. Any of these terms or job titles can be used interchangeably with the user of the systems disclosed herein unless otherwise explicitly demarcated. For example, a reference to a surgeon also could apply, in some embodiments to a technician or nurse.

The systems, methods, and devices disclosed herein are particularly well adapted for surgical procedures that utilize surgical navigation systems, such as the CORI® surgical navigation system. CORI is a registered trademark of SMITH & NEPHEW, INC. of Memphis, TN.

CASS Ecosystem Overview

Figure 1:
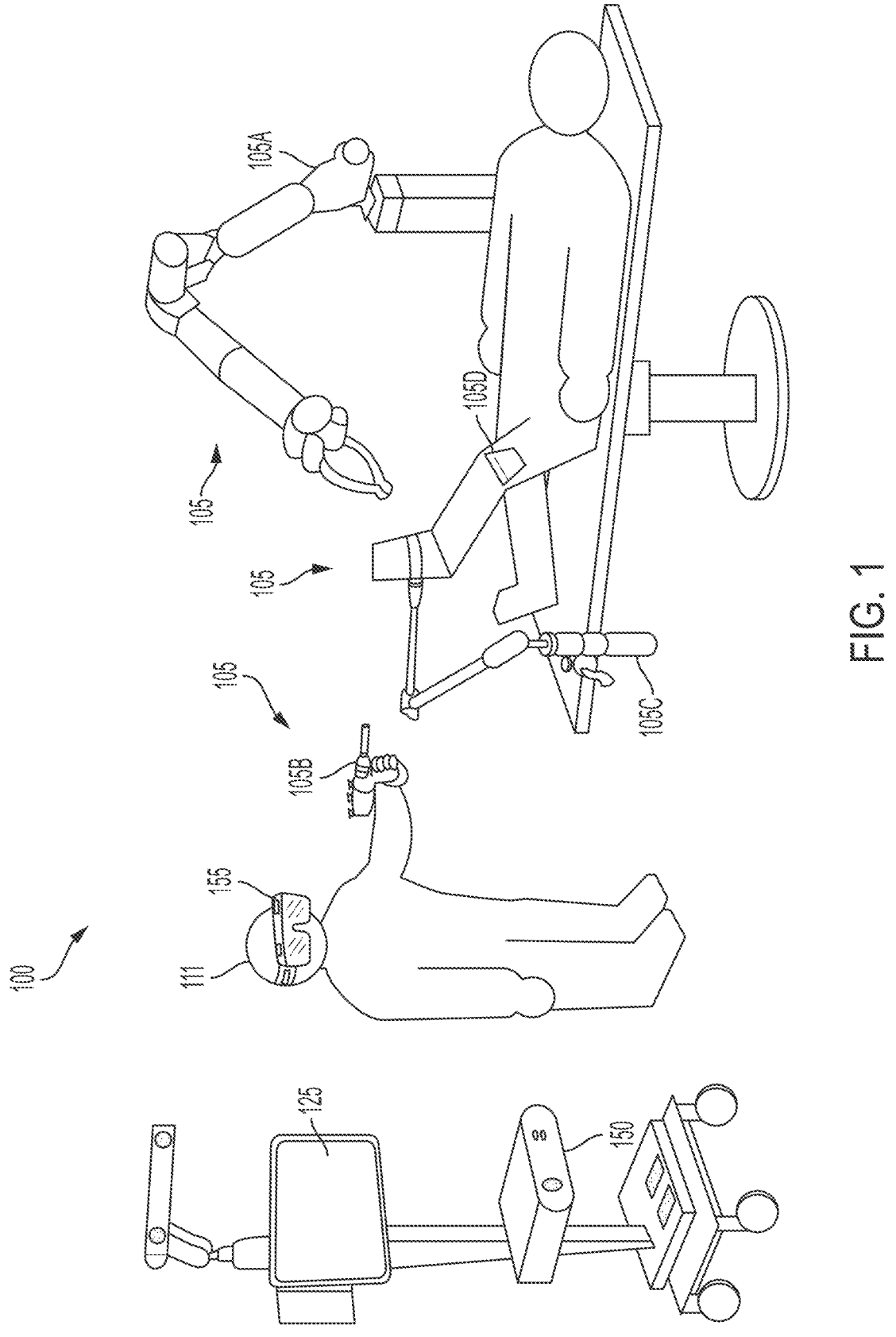
FIG. 1 depicts an operating theatre including an illustrative computer-assisted surgical system (CASS) in accordance with an embodiment.

FIG. 1 provides an illustration of an example computer-assisted surgical system (CASS) 100, according to some embodiments. As described in further detail in the sections that follow, the CASS uses computers, robotics, and imaging technology to aid surgeons in performing orthopedic surgery procedures such as total knee arthroplasty (TKA) or total hip arthroplasty (THA). For example, surgical navigation systems can aid surgeons in locating patient anatomical structures, guiding surgical instruments, and implanting medical devices with a high degree of accuracy. Surgical navigation systems such as the CASS 100 often employ various forms of computing technology to perform a wide variety of standard and minimally invasive surgical procedures and techniques. Moreover, these systems allow surgeons to more accurately plan, track and navigate the placement of instruments and implants relative to the body of a patient, as well as conduct pre-operative and intra-operative body imaging.

An Effector Platform 105 positions surgical tools relative to a patient during surgery. The exact components of the Effector Platform 105 will vary, depending on the embodiment employed. For example, for a knee surgery, the Effector Platform 105 may include an End Effector 105B that holds surgical tools or instruments during their use. The End Effector 105B may be a handheld device or instrument used by the surgeon (e.g., a CORI® hand piece or a cutting guide or jig) or, alternatively, the End Effector 105B can include a device or instrument held or positioned by a Robotic Arm 105A. While one Robotic Arm 105A is illustrated in FIG. 1, in some embodiments there may be multiple devices. As examples, there may be one Robotic Arm 105A on each side of an operating table T or two devices on one side of the table T. The Robotic Arm 105A may be mounted directly to the table T, be located next to the table T on a floor platform (not shown), mounted on a floor-to-ceiling pole, or mounted on a wall or ceiling of an operating room. The floor platform may be fixed or moveable. In one particular embodiment, the robotic arm 105A is mounted on a floor-to-ceiling pole located between the patient's legs or feet. In some embodiments, the End Effector 105B may include a suture holder or a stapler to assist in closing wounds. Further, in the case of two robotic arms 105A, the surgical computer 150 can drive the robotic arms 105A to work together to suture the wound at closure. Alternatively, the surgical computer 150 can drive one or more robotic arms 105A to staple the wound at closure.

The Effector Platform 105 can include a Limb Positioner 105C for positioning the patient's limbs during surgery. One example of a Limb Positioner 105C is the SMITH AND NEPHEW SPIDER2 system. The Limb Positioner 105C may be operated manually by the surgeon or alternatively change limb positions based on instructions received from the Surgical Computer 150 (described below). While one Limb Positioner 105C is illustrated in FIG. 1, in some embodiments there may be multiple devices. As examples, there may be one Limb Positioner 105C on each side of the operating table T or two devices on one side of the table T. The Limb Positioner 105C may be mounted directly to the table T, be located next to the table T on a floor platform (not shown), mounted on a pole, or mounted on a wall or ceiling of an operating room. In some embodiments, the Limb Positioner 105C can be used in non-conventional ways, such as a retractor or specific bone holder. The Limb Positioner 105C may include, as examples, an ankle boot, a soft tissue clamp, a bone clamp, or a soft-tissue retractor spoon, such as a hooked, curved, or angled blade. In some embodiments, the Limb Positioner 105C may include a suture holder to assist in closing wounds.

The Effector Platform 105 may include tools, such as a screwdriver, light or laser, to indicate an axis or plane, bubble level, pin driver, pin puller, plane checker, pointer, finger, or some combination thereof.

Resection Equipment 110 (not shown in FIG. 1) performs bone or tissue resection using, for example, mechanical, ultrasonic, or laser techniques. Examples of Resection Equipment 110 include drilling devices, burring devices, oscillatory sawing devices, vibratory impaction devices, reamers, ultrasonic bone cutting devices, radio frequency ablation devices, reciprocating devices (such as a rasp or broach), and laser ablation systems. In some embodiments, the Resection Equipment 110 is held and operated by the surgeon during surgery. In other embodiments, the Effector Platform 105 may be used to hold the Resection Equipment 110 during use.

The Effector Platform 105 also can include a cutting guide or jig 105D that is used to guide saws or drills used to resect tissue during surgery. Such cutting guides 105D can be formed integrally as part of the Effector Platform 105 or Robotic Arm 105A, or cutting guides can be separate structures that can be matingly and/or removably attached to the Effector Platform 105 or Robotic Arm 105A. The Effector Platform 105 or Robotic Arm 105A can be controlled by the CASS 100 to position a cutting guide or jig 105D adjacent to the patient's anatomy in accordance with a pre-operatively or intraoperatively developed surgical plan such that the cutting guide or jig will produce a precise bone cut in accordance with the surgical plan.

The Tracking System 115 uses one or more sensors to collect real-time position data that locates the patient's anatomy and surgical instruments. For example, for TKA procedures, the Tracking System may provide a location and orientation of the End Effector 105B during the procedure.

In addition to positional data, data from the Tracking System 115 also can be used to infer velocity/acceleration of anatomy/instrumentation, which can be used for tool control. In some embodiments, the Tracking System 115 may use a tracker array attached to the End Effector 105B to determine the location and orientation of the End Effector 105B. The position of the End Effector 105B may be inferred based on the position and orientation of the Tracking System 115 and a known relationship in three-dimensional space between the Tracking System 115 and the End Effector 105B. Various types of tracking systems may be used in various embodiments of the present invention including, without limitation, Infrared (IR) tracking systems, electromagnetic (EM) tracking systems, video or image based tracking systems, and ultrasound registration and tracking systems. Using the data provided by the tracking system 115, the surgical computer 150 can detect objects and prevent collision. For example, the surgical computer 150 can prevent the Robotic Arm 105A and/or the End Effector 105B from colliding with soft tissue.

Any suitable tracking system can be used for tracking surgical objects and patient anatomy in the surgical theatre. For example, a combination of IR and visible light cameras can be used in an array. Various illumination sources, such as an IR LED light source, can illuminate the scene allowing three-dimensional imaging to occur. In some embodiments, this can include stereoscopic, tri-scopic, quad-scopic, etc. imaging. In addition to the camera array, which in some embodiments is affixed to a cart, additional cameras can be placed throughout the surgical theatre. For example, handheld tools or headsets worn by operators/surgeons can include imaging capability that communicates images back to a central processor to correlate those images with images captured by the camera array. This can give a more robust image of the environment for modeling using multiple perspectives. Furthermore, some imaging devices may be of suitable resolution or have a suitable perspective on the scene to pick up information stored in quick response (QR) codes or barcodes. This can be helpful in identifying specific objects not manually registered with the system. In some embodiments, the camera may be mounted on the Robotic Arm 105A.

Although, as discussed herein, the majority of tracking and/or navigation techniques utilize image-based tracking systems (e.g., IR tracking systems, video or image based tracking systems, etc.). However, electromagnetic (EM) based tracking systems are becoming more common for a variety of reasons. For example, implantation of standard optical trackers requires tissue resection (e.g., down to the cortex) as well as subsequent drilling and driving of cortical pins. Additionally, because optical trackers require a direct line of sight with a tracking system, the placement of such trackers may need to be far from the surgical site to ensure they do not restrict the movement of a surgeon or medical professional.

In some embodiments, specific objects can be manually registered by a surgeon with the system preoperatively or intraoperatively. For example, by interacting with a user interface, a surgeon may identify the starting location for a tool or a bone structure. By tracking fiducial marks associated with that tool or bone structure, or by using other conventional image tracking modalities, a processor may track that tool or bone as it moves through the environment in a three-dimensional model.

In some embodiments, certain markers, such as fiducial marks that identify individuals, important tools, or bones in the theater may include passive or active identifiers that can be picked up by a camera or camera array associated with the tracking system. For example, an IR LED can flash a pattern that conveys a unique identifier to the source of that pattern, providing a dynamic identification mark. Similarly, one or two dimensional optical codes (barcode, QR code, etc.) can be affixed to objects in the theater to provide passive identification that can occur based on image analysis. If these codes are placed asymmetrically on an object, they also can be used to determine an orientation of an object by comparing the location of the identifier with the extents of an object in an image. For example, a QR code may be placed in a corner of a tool tray, allowing the orientation and identity of that tray to be tracked. Other tracking modalities are explained throughout. For example, in some embodiments, augmented reality headsets can be worn by surgeons and other staff to provide additional camera angles and tracking capabilities.

In addition to optical tracking, certain features of objects can be tracked by registering physical properties of the object and associating them with objects that can be tracked, such as fiducial marks fixed to a tool or bone. For example, a surgeon may perform a manual registration process whereby a tracked tool and a tracked bone can be manipulated relative to one another. By impinging the tip of the tool against the surface of the bone, a three-dimensional surface can be mapped for that bone that is associated with a position and orientation relative to the frame of reference of that fiducial mark. By optically tracking the position and orientation (pose) of the fiducial mark associated with that bone, a model of that surface can be tracked with an environment through extrapolation.

The registration process that registers the CASS 100 to the relevant anatomy of the patient also can involve the use of anatomical landmarks, such as landmarks on a bone or cartilage. For example, the CASS 100 can include a 3D model of the relevant bone or joint and the surgeon can intraoperatively collect data regarding the location of bony landmarks on the patient's actual bone using a probe that is connected to the CASS. Bony landmarks can include, for example, the medial malleolus and lateral malleolus, the ends of the proximal femur and distal tibia, and the center of the hip joint. The CASS 100 can compare and register the location data of bony landmarks collected by the surgeon with the probe with the location data of the same landmarks in the 3D model. Alternatively, the CASS 100 can construct a 3D model of the bone or joint without pre-operative image data by using location data of bony landmarks and the bone surface that are collected by the surgeon using a CASS probe or other means. The registration process also can include determining various axes of a joint. For example, for a TKA the surgeon can use the CASS 100 to determine the anatomical and mechanical axes of the femur and tibia. The surgeon and the CASS 100 can identify the center of the hip joint by moving the patient's leg in a spiral direction (i.e., circumduction) so the CASS can determine where the center of the hip joint is located.

A Tissue Navigation System 120 (not shown in FIG. 1) provides the surgeon with intraoperative, real-time visualization for the patient's bone, cartilage, muscle, nervous, and/or vascular tissues surrounding the surgical area. Examples of systems that may be employed for tissue navigation include fluorescent imaging systems and ultrasound systems.

The Display 125 provides graphical user interfaces (GUIs) that display images collected by the Tissue Navigation System 120 as well other information relevant to the surgery. For example, in one embodiment, the Display 125 overlays image information collected from various modalities (e.g., CT, MRI, X-ray, fluorescent, ultrasound, etc.) collected pre-operatively or intra-operatively to give the surgeon various views of the patient's anatomy as well as real-time conditions. The Display 125 may include, for example, one or more computer monitors. As an alternative or supplement to the Display 125, one or more members of the surgical staff may wear an Augmented Reality (AR) Head Mounted Device (HMD). For example, in FIG. 1 the Surgeon 111 is wearing an AR HMD 155 that may, for example, overlay pre-operative image data on the patient or provide surgical planning suggestions. Various example uses of the AR HMD 155 in surgical procedures are detailed in the sections that follow.

Surgical Computer 150 provides control instructions to various components of the CASS 100, collects data from those components, and provides general processing for various data needed during surgery. In some embodiments, the Surgical Computer 150 is a general purpose computer. In other embodiments, the Surgical Computer 150 may be a parallel computing platform that uses multiple central processing units (CPUs) or graphics processing units (GPU) to perform processing. In some embodiments, the Surgical Computer 150 is connected to a remote server over one or more computer networks (e.g., the Internet). The remote server can be used, for example, for storage of data or execution of computationally intensive processing tasks.

Various techniques generally known in the art can be used for connecting the Surgical Computer 150 to the other components of the CASS 100. Moreover, the computers can connect to the Surgical Computer 150 using a mix of technologies. For example, the End Effector 105B may connect to the Surgical Computer 150 over a wired (i.e., serial) connection. The Tracking System 115, Tissue Navigation System 120, and Display 125 can similarly be connected to the Surgical Computer 150 using wired connections. Alternatively, the Tracking System 115, Tissue Navigation System 120, and Display 125 may connect to the Surgical Computer 150 using wireless technologies such as, without limitation, Wi-Fi, Bluetooth, Near Field Communication (NFC), or ZigBee.

Powered Impaction and Acetabular Reamer Devices

Part of the flexibility of the CASS design described above with respect to FIG. 1 is that additional or alternative devices can be added to the CASS 100 as necessary to support particular surgical procedures. For example, in the context of hip surgeries, the CASS 100 may include a powered impaction device. Impaction devices are designed to repeatedly apply an impaction force that the surgeon can use to perform activities such as implant alignment. For example, within a total hip arthroplasty (THA), a surgeon will often insert a prosthetic acetabular cup into the implant host's acetabulum using an impaction device. Although impaction devices can be manual in nature (e.g., operated by the surgeon striking an impactor with a mallet), powered impaction devices are generally easier and quicker to use in the surgical setting. Powered impaction devices may be powered, for example, using a battery attached to the device. Various attachment pieces may be connected to the powered impaction device to allow the impaction force to be directed in various ways as needed during surgery. Also, in the context of hip surgeries, the CASS 100 may include a powered, robotically controlled end effector to ream the acetabulum to accommodate an acetabular cup implant.

In a robotically-assisted THA, the patient's anatomy can be registered to the CASS 100 using CT or other image data, the identification of anatomical landmarks, tracker arrays attached to the patient's bones, and one or more cameras. Tracker arrays can be mounted on the iliac crest using clamps and/or bone pins and such trackers can be mounted externally through the skin or internally (either posterolaterally or anterolaterally) through the incision made to perform the THA. For a THA, the CASS 100 can utilize one or more femoral cortical screws inserted into the proximal femur as checkpoints to aid in the registration process. The CASS 100 also can utilize one or more checkpoint screws inserted into the pelvis as additional checkpoints to aid in the registration process. Femoral tracker arrays can be secured to or mounted in the femoral cortical screws. The CASS 100 can employ steps where the registration is verified using a probe that the surgeon precisely places on key areas of the proximal femur and pelvis identified for the surgeon on the display 125. Trackers can be located on the robotic arm 105A or end effector 105B to register the arm and/or end effector to the CASS 100. The verification step also can utilize proximal and distal femoral checkpoints. The CASS 100 can utilize color prompts or other prompts to inform the surgeon that the registration process for the relevant bones and the robotic arm 105A or end effector 105B has been verified to a certain degree of accuracy (e.g., within 1 mm).

For a THA, the CASS 100 can include a broach tracking option using femoral arrays to allow the surgeon to intra-operatively capture the broach position and orientation and calculate hip length and offset values for the patient. Based on information provided about the patient's hip joint and the planned implant position and orientation after broach tracking is completed, the surgeon can make modifications or adjustments to the surgical plan.

For a robotically-assisted THA, the CASS 100 can include one or more powered reamers connected or attached to a robotic arm 105A or end effector 105B that prepares the pelvic bone to receive an acetabular implant according to a surgical plan. The robotic arm 105A and/or end effector 105B can inform the surgeon and/or control the power of the reamer to ensure that the acetabulum is being resected (reamed) in accordance with the surgical plan. For example, if the surgeon attempts to resect bone outside of the boundary of the bone to be resected in accordance with the surgical plan, the CASS 100 can power off the reamer or instruct the surgeon to power off the reamer. The CASS 100 can provide the surgeon with an option to turn off or disengage the robotic control of the reamer. The display 125 can depict the progress of the bone being resected (reamed) as compared to the surgical plan using different colors. The surgeon can view the display of the bone being resected (reamed) to guide the reamer to complete the reaming in accordance with the surgical plan. The CASS 100 can provide visual or audible prompts to the surgeon to warn the surgeon that resections are being made that are not in accordance with the surgical plan.

Following reaming, the CASS 100 can employ a manual or powered impactor that is attached or connected to the robotic arm 105A or end effector 105B to impact trial implants and final implants into the acetabulum. The robotic arm 105A and/or end effector 105B can be used to guide the impactor to impact the trial and final implants into the acetabulum in accordance with the surgical plan. The CASS 100 can cause the position and orientation of the trial and final implants vis-à-vis the bone to be displayed to inform the surgeon as to how the trial and final implant's orientation and position compare to the surgical plan, and the display 125 can show the implant's position and orientation as the surgeon manipulates the leg and hip. The CASS 100 can provide the surgeon with the option of re-planning and re-doing the reaming and implant impaction by preparing a new surgical plan if the surgeon is not satisfied with the original implant position and orientation.

Preoperatively, the CASS 100 can develop a proposed surgical plan based on a three dimensional model of the hip joint and other information specific to the patient, such as the mechanical and anatomical axes of the leg bones, the epicondylar axis, the femoral neck axis, the dimensions (e.g., length) of the femur and hip, the midline axis of the hip joint, the ASIS axis of the hip joint, and the location of anatomical landmarks such as the lesser trochanter landmarks, the distal landmark, and the center of rotation of the hip joint. The CASS-developed surgical plan can provide a recommended optimal implant size and implant position and orientation based on the three dimensional model of the hip joint and other information specific to the patient. The CASS-developed surgical plan can include proposed details on offset values, inclination and anteversion values, center of rotation, cup size, medialization values, superior-inferior fit values, femoral stem sizing and length.

For a THA, the CASS-developed surgical plan can be viewed preoperatively and intraoperatively, and the surgeon can modify CASS-developed surgical plan preoperatively or intraoperatively. The CASS-developed surgical plan can display the planned resection to the hip joint and superimpose the planned implants onto the hip joint based on the planned resections. The CASS 100 can provide the surgeon with options for different surgical workflows that will be displayed to the surgeon based on a surgeon's preference. For example, the surgeon can choose from different workflows based on the number and types of anatomical landmarks that are checked and captured and/or the location and number of tracker arrays used in the registration process.

According to some embodiments, a powered impaction device used with the CASS 100 may operate with a variety of different settings. In some embodiments, the surgeon adjusts settings through a manual switch or other physical mechanism on the powered impaction device. In other embodiments, a digital interface may be used that allows setting entry, for example, via a touchscreen on the powered impaction device. Such a digital interface may allow the available settings to vary based, for example, on the type of attachment piece connected to the power attachment device. In some embodiments, rather than adjusting the settings on the powered impaction device itself, the settings can be changed through communication with a robot or other computer system within the CASS 100. Such connections may be established using, for example, a Bluetooth or Wi-Fi networking module on the powered impaction device. In another embodiment, the impaction device and end pieces may contain features that allow the impaction device to be aware of what end piece (cup impactor, broach handle, etc.) is attached with no action required by the surgeon, and adjust the settings accordingly. This may be achieved, for example, through a QR code, barcode, RFID tag, or other method.

Examples of the settings that may be used include cup impaction settings (e.g., single direction, specified frequency range, specified force and/or energy range); broach impaction settings (e.g., dual direction/oscillating at a specified frequency range, specified force and/or energy range); femoral head impaction settings (e.g., single direction/single blow at a specified force or energy); and stem impaction settings (e.g., single direction at specified frequency with a specified force or energy). Additionally, in some embodiments, the powered impaction device includes settings related to acetabular liner impaction (e.g., single direction/single blow at a specified force or energy). There may be a plurality of settings for each type of liner such as poly, ceramic, oxinium, or other materials. Furthermore, the powered impaction device may offer settings for different bone quality based on preoperative testing/imaging/knowledge and/or intraoperative assessment by surgeon. In some embodiments, the powered impactor device may have a dual function. For example, the powered impactor device not only could provide reciprocating motion to provide an impact force, but also could provide reciprocating motion for a broach or rasp.

In some embodiments, the powered impaction device includes feedback sensors that gather data during instrument use and send data to a computing device, such as a controller within the device or the Surgical Computer 150. This computing device can then record the data for later analysis and use. Examples of the data that may be collected include, without limitation, sound waves, the predetermined resonance frequency of each instrument, reaction force or rebound energy from patient bone, location of the device with respect to imaging (e.g., fluoro, CT, ultrasound, MRI, etc.) registered bony anatomy, and/or external strain gauges on bones.

Once the data is collected, the computing device may execute one or more algorithms in real-time or near real-time to aid the surgeon in performing the surgical procedure. For example, in some embodiments, the computing device uses the collected data to derive information such as the proper final broach size (femur); when the stem is fully seated (femur side); or when the cup is seated (depth and/or orientation) for a THA. Once the information is known, it may be displayed for the surgeon's review, or it may be used to activate haptics or other feedback mechanisms to guide the surgical procedure.

Additionally, the data derived from the aforementioned algorithms may be used to drive operation of the device. For example, during insertion of a prosthetic acetabular cup with a powered impaction device, the device may automatically extend an impaction head (e.g., an end effector) moving the implant into the proper location, or turn the power off to the device once the implant is fully seated. In one embodiment, the derived information may be used to automatically adjust settings for quality of bone where the powered impaction device should use less power to mitigate femoral/acetabular/pelvic fracture or damage to surrounding tissues.

Robotic Arm

In some embodiments, the CASS 100 includes a robotic arm 105A that serves as an interface to stabilize and hold a variety of instruments used during the surgical procedure. For example, in the context of a hip surgery, these instruments may include, without limitation, retractors, a sagittal or reciprocating saw, the reamer handle, the cup impactor, the broach handle, and the stem inserter. The robotic arm 105A may have multiple degrees of freedom (like a Spider device), and have the ability to be locked in place (e.g., by a press of a button, voice activation, a surgeon removing a hand from the robotic arm, or other method).

In some embodiments, movement of the robotic arm 105A may be effectuated by use of a control panel built into the robotic arm system. For example, a display screen may include one or more input sources, such as physical buttons or a user interface having one or more icons, that direct movement of the robotic arm 105A. The surgeon or other healthcare professional may engage with the one or more input sources to position the robotic arm 105A when performing a surgical procedure.

A tool or an end effector 105B attached or integrated into a robotic arm 105A may include, without limitation, a burring device, a scalpel, a cutting device, a retractor, a joint tensioning device, or the like. In embodiments in which an end effector 105B is used, the end effector may be positioned at the end of the robotic arm 105A such that any motor control operations are performed within the robotic arm system. In embodiments in which a tool is used, the tool may be secured at a distal end of the robotic arm 105A, but motor control operation may reside within the tool itself.

The robotic arm 105A may be motorized internally to both stabilize the robotic arm, thereby preventing it from falling and hitting the patient, surgical table, surgical staff, etc., and to allow the surgeon to move the robotic arm without having to fully support its weight. While the surgeon is moving the robotic arm 105A, the robotic arm may provide some resistance to prevent the robotic arm from moving too fast or having too many degrees of freedom active at once. The position and the lock status of the robotic arm 105A may be tracked, for example, by a controller or the Surgical Computer 150.

In some embodiments, the robotic arm 105A can be moved by hand (e.g., by the surgeon) or with internal motors into its ideal position and orientation for the task being performed. In some embodiments, the robotic arm 105A may be enabled to operate in a "free" mode that allows the surgeon to position the arm into a desired position without being restricted. While in the free mode, the position and orientation of the robotic arm 105A may still be tracked as described above. In one embodiment, certain degrees of freedom can be selectively released upon input from user (e.g., surgeon) during specified portions of the surgical plan tracked by the Surgical Computer 150. Designs in which a robotic arm 105A is internally powered through hydraulics or motors or provides resistance to external manual motion through similar means can be described as powered robotic arms, while arms that are manually manipulated without power feedback, but which may be manually or automatically locked in place, may be described as passive robotic arms.

A robotic arm 105A or end effector 105B can include a trigger or other means to control the power of a saw or drill. Engagement of the trigger or other means by the surgeon can cause the robotic arm 105A or end effector 105B to transition from a motorized alignment mode to a mode where the saw or drill is engaged and powered on. Additionally, the CASS 100 can include a foot pedal (not shown) that causes the system to perform certain functions when activated. For example, the surgeon can activate the foot pedal to instruct the CASS 100 to place the robotic arm 105A or end effector 105B in an automatic mode that brings the robotic arm or end effector into the proper position with respect to the patient's anatomy in order to perform the necessary resections. The CASS 100 also can place the robotic arm 105A or end effector 105B in a collaborative mode that allows the surgeon to manually manipulate and position the robotic arm or end effector into a particular location. The collaborative mode can be configured to allow the surgeon to move the robotic arm 105A or end effector 105B medially or laterally, while restricting movement in other directions. As discussed, the robotic arm 105A or end effector 105B can include a cutting device (saw, drill, and burr) or a cutting guide or jig 105D that will guide a cutting device. In other embodiments, movement of the robotic arm 105A or robotically controlled end effector 105B can be controlled entirely by the CASS 100 without any, or with only minimal, assistance or input from a surgeon or other medical professional. In still other embodiments, the movement of the robotic arm 105A or robotically controlled end effector 105B can be controlled remotely by a surgeon or other medical professional using a control mechanism separate from the robotic arm or robotically controlled end effector device, for example using a joystick or interactive monitor or display control device.

A robotic arm 105A may be used for holding the retractor. For example, in one embodiment, the robotic arm 105A may be moved into the desired position by the surgeon. At that point, the robotic arm 105A may lock into place. In some embodiments, the robotic arm 105A is provided with data regarding the patient's position, such that if the patient moves, the robotic arm can adjust the retractor position accordingly. In some embodiments, multiple robotic arms may be used, thereby allowing multiple retractors to be held or for more than one activity to be performed simultaneously (e.g., retractor holding & reaming).

The robotic arm 105A may also be used to help stabilize the surgeon's hand while making a femoral neck cut. In this application, control of the robotic arm 105A may impose certain restrictions to prevent soft tissue damage from occurring. For example, in one embodiment, the Surgical Computer 150 tracks the position of the robotic arm 105A as it operates. If the tracked location approaches an area where tissue damage is predicted, a command may be sent to the robotic arm 105A causing it to stop. Alternatively, where the robotic arm 105A is automatically controlled by the Surgical Computer 150, the Surgical Computer may ensure that the robotic arm is not provided with any instructions that cause it to enter areas where soft tissue damage is likely to occur. The Surgical Computer 150 may impose certain restrictions on the surgeon to prevent the surgeon from reaming too far into the medial wall of the acetabulum or reaming at an incorrect angle or orientation.

In some embodiments, the robotic arm 105A may be used to hold a cup impactor at a desired angle or orientation during cup impaction. When the final position has been achieved, the robotic arm 105A may prevent any further seating to prevent damage to the pelvis.

The surgeon may use the robotic arm 105A to position the broach handle at the desired position and allow the surgeon to impact the broach into the femoral canal at the desired orientation. In some embodiments, once the Surgical Computer 150 receives feedback that the broach is fully seated, the robotic arm 105A may restrict the handle to prevent further advancement of the broach.

The robotic arm 105A may also be used for resurfacing applications. For example, the robotic arm 105A may stabilize the surgeon while using traditional instrumentation and provide certain restrictions or limitations to allow for proper placement of implant components (e.g., guide wire placement, chamfer cutter, sleeve cutter, plan cutter, etc.). Where only a burr is employed, the robotic arm 105A may stabilize the surgeon's handpiece and may impose restrictions on the handpiece to prevent the surgeon from removing unintended bone in contravention of the surgical plan.

The robotic arm 105A may be a passive arm. As an example, the robotic arm 105A may be a CIRQ robot arm available from Brainlab AG. CIRQ is a registered trademark of Brainlab AG, Olof-Palme-Str. 9 81829, München, FED REP of GERMANY. In one particular embodiment, the robotic arm 105A is an intelligent holding arm as disclosed in U.S. patent application Ser. No. 15/525,585 to Krinninger et al., U.S. patent application Ser. No. 15/561,042 to Nowatschin et al., U.S. patent application Ser. No. 15/561, 048 to Nowatschin et al., and U.S. Pat. No. 10,342,636 to Nowatschin et al., the entire contents of each of which is herein incorporated by reference.

Surgical Procedure Data Generation and Collection

The various services that are provided by medical professionals to treat a clinical condition are collectively referred to as an "episode of care." For a particular surgical intervention the episode of care can include three phases: pre-operative, intra-operative, and post-operative. During each phase, data is collected or generated that can be used to analyze the episode of care in order to understand various features of the procedure and identify patterns that may be used, for example, in training models to make decisions with minimal human intervention. The data collected over the episode of care may be stored at the Surgical Computer 150 or the Surgical Data Server 180 as a complete dataset. Thus, for each episode of care, a dataset exists that comprises all of the data collectively pre-operatively about the patient, all of the data collected or stored by the CASS 100 intra-operatively, and any post-operative data provided by the patient or by a healthcare professional monitoring the patient.

As explained in further detail, the data collected during the episode of care may be used to enhance performance of the surgical procedure or to provide a holistic understanding of the surgical procedure and the patient outcomes. For example, in some embodiments, the data collected over the episode of care may be used to generate a surgical plan. In one embodiment, a high-level, pre-operative plan is refined intra-operatively as data is collected during surgery. In this way, the surgical plan can be viewed as dynamically changing in real-time or near real-time as new data is collected by the components of the CASS 100. In other embodiments, pre-operative images or other input data may be used to develop a robust plan preoperatively that is simply executed during surgery. In this case, the data collected by the CASS 100 during surgery may be used to make recommendations that ensure that the surgeon stays within the pre-operative surgical plan. For example, if the surgeon is unsure how to achieve a certain prescribed cut or implant alignment, the Surgical Computer 150 can be queried for a recommendation. In still other embodiments, the pre-operative and intra-operative planning approaches can be combined such that a robust pre-operative plan can be dynamically modified, as necessary or desired, during the surgical procedure. In some embodiments, a biomechanics-based model of patient anatomy contributes simulation data to be considered by the CASS 100 in developing preoperative, intraoperative, and post-operative/rehabilitation procedures to optimize implant performance outcomes for the patient.

Aside from changing the surgical procedure itself, the data gathered during the episode of care may be used as an input to other procedures ancillary to the surgery. For example, in some embodiments, implants can be designed using episode of care data. Example data-driven techniques for designing, sizing, and fitting implants are described in U.S. patent application Ser. No. 13/814,531 filed Aug. 15, 2011 and entitled "Systems and Methods for Optimizing Parameters for Orthopaedic Procedures"; U.S. patent application Ser. No. 14/232,958 filed Jul. 20, 2012 and entitled "Systems and Methods for Optimizing Fit of an Implant to Anatomy"; and U.S. patent application Ser. No. 12/234,444 filed Sep. 19, 2008 and entitled "Operatively Tuning Implants for Increased Performance," the entire contents of each of which are hereby incorporated by reference into this patent application.

Furthermore, the data can be used for educational, training, or research purposes. For example, using the network-based approach described below in FIG. 5C, other doctors or students can remotely view surgeries in interfaces that allow them to selectively view data as it is collected from the various components of the CASS 100. After the surgical procedure, similar interfaces may be used to "playback" a surgery for training or other educational purposes, or to identify the source of any issues or complications with the procedure.

Data acquired during the pre-operative phase generally includes all information collected or generated prior to the surgery. Thus, for example, information about the patient may be acquired from a patient intake form or electronic medical record (EMR). Examples of patient information that may be collected include, without limitation, patient demographics, diagnoses, medical histories, progress notes, vital signs, medical history information, allergies, and lab results. The pre-operative data may also include images related to the anatomical area of interest. These images may be captured, for example, using Magnetic Resonance Imaging (MRI), Computed Tomography (CT), X-ray, ultrasound, or any other modality known in the art. The pre-operative data may also comprise quality of life data captured from the patient. For example, in one embodiment, pre-surgery patients use a mobile application ("app") to answer questionnaires regarding their current quality of life. In some embodiments, preoperative data used by the CASS 100 includes demographic, anthropometric, cultural, or other specific traits about a patient that can coincide with activity levels and specific patient activities to customize the surgical plan to the patient. For example, certain cultures or demographics may be more likely to use a toilet that requires squatting on a daily basis.

Figure 2A:
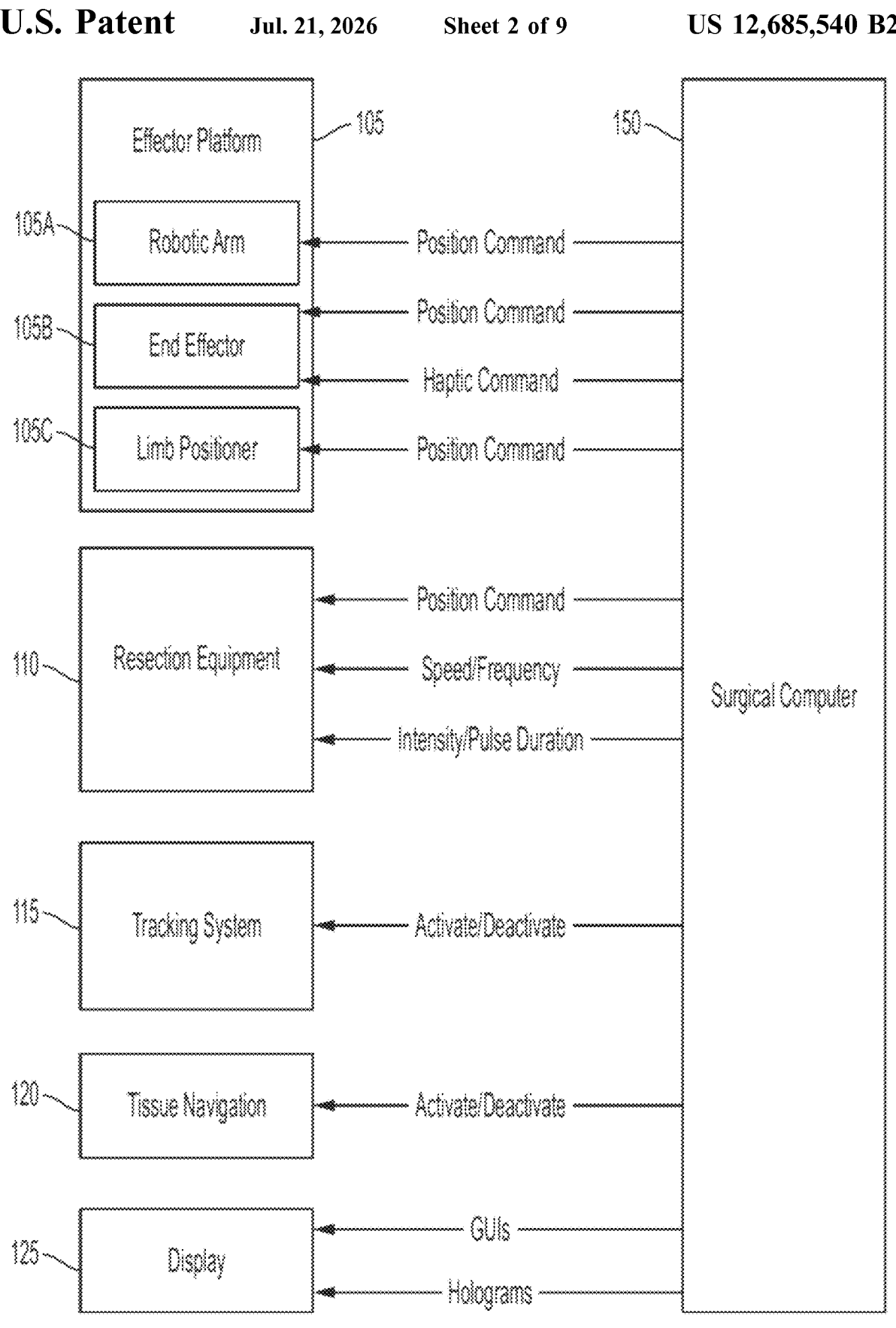
FIG. 2A depicts illustrative control instructions that a surgical computer provides to other components of a CASS in accordance with an embodiment.
Figure 2B:
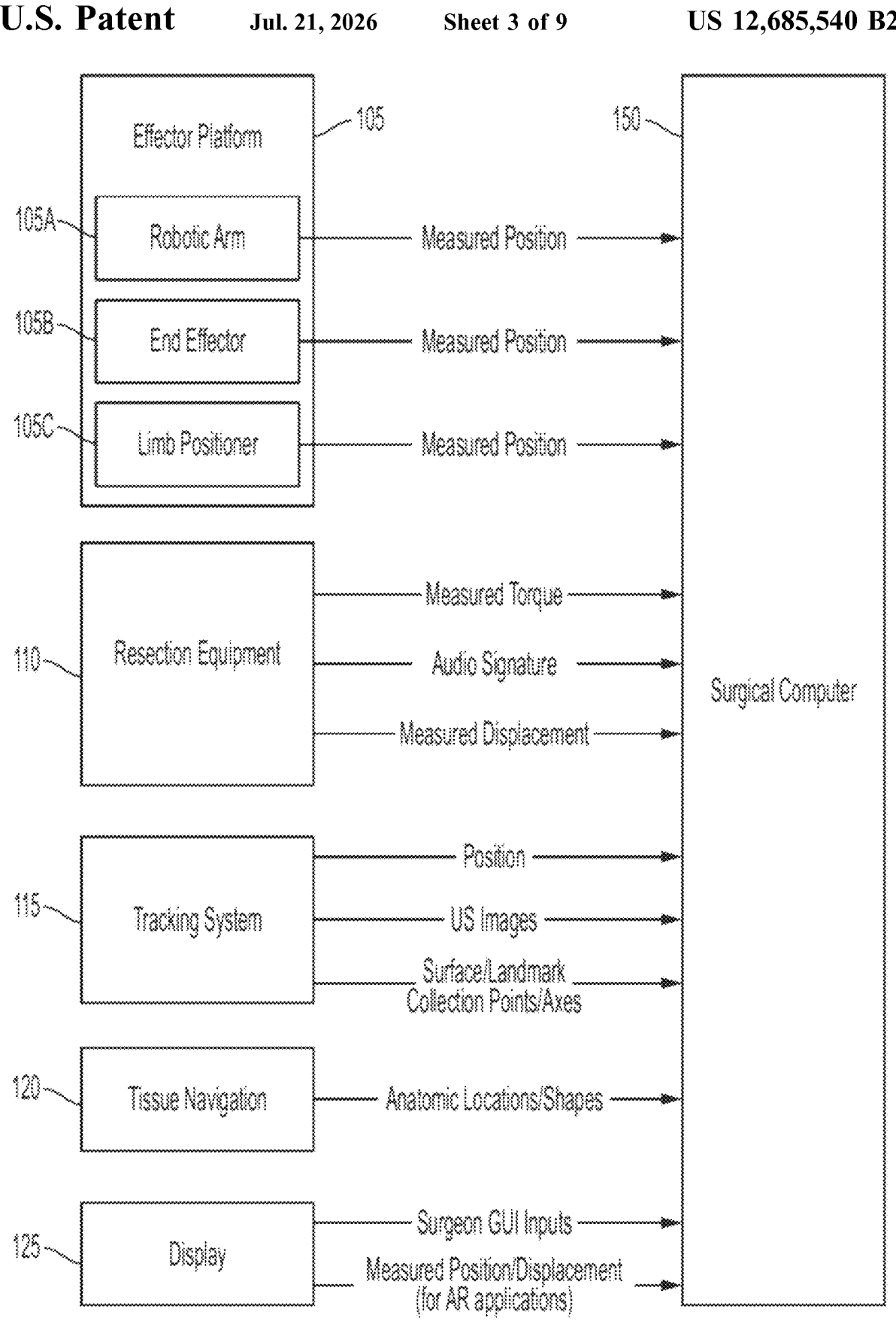
FIG. 2B depicts illustrative control instructions that components of a CASS provide to a surgical computer in accordance with an embodiment.

FIGS. 2A and 2B provide examples of data that may be acquired during the intra-operative phase of an episode of care. These examples are based on the various components of the CASS 100 described above with reference to FIG. 1; however, it should be understood that other types of data may be used based on the types of equipment used during surgery and their use.

FIG. 2A shows examples of some of the control instructions that the Surgical Computer 150 provides to other components of the CASS 100, according to some embodiments. Note that the example of FIG. 2A assumes that the components of the Effector Platform 105 are each controlled directly by the Surgical Computer 150. In embodiments where a component is manually controlled by the Surgeon 111, instructions may be provided on the Display 125 or AR HMD 155 instructing the Surgeon 111 how to move the component.

The various components included in the Effector Platform 105 are controlled by the Surgical Computer 150 providing position commands that instruct the component where to move within a coordinate system. In some embodiments, the Surgical Computer 150 provides the Effector Platform 105 with instructions defining how to react when a component of the Effector Platform 105 deviates from a surgical plan. These commands are referenced in FIG. 2A as "haptic" commands. For example, the End Effector 105B may provide a force to resist movement outside of an area where resection is planned. Other commands that may be used by the Effector Platform 105 include vibration and audio cues.

In some embodiments, the end effectors 105B of the robotic arm 105A are operatively coupled with cutting guide 105D. In response to an anatomical model of the surgical scene, the robotic arm 105A can move the end effectors 105B and the cutting guide 105D into position to match the location of the femoral or tibial cut to be performed in accordance with the surgical plan. This can reduce the likelihood of error, allowing the vision system and a processor utilizing that vision system to implement the surgical plan to place a cutting guide 105D at the precise location and orientation relative to the tibia or femur to align a cutting slot of the cutting guide with the cut to be performed according to the surgical plan. Then, a surgeon can use any suitable tool, such as an oscillating or rotating saw or drill to perform the cut (or drill a hole) with perfect placement and orientation because the tool is mechanically limited by the features of the cutting guide 105D. In some embodiments, the cutting guide 105D may include one or more pin holes that are used by a surgeon to drill and screw or pin the cutting guide into place before performing a resection of the patient tissue using the cutting guide. This can free the robotic arm 105A or ensure that the cutting guide 105D is fully affixed without moving relative to the bone to be resected. For example, this procedure can be used to make the first distal cut of the femur during a total knee arthroplasty. In some embodiments, where the arthroplasty is a hip arthroplasty, cutting guide 105D can be fixed to the femoral head or the acetabulum for the respective hip arthroplasty resection. It should be understood that any arthroplasty that utilizes precise cuts can use the robotic arm 105A and/or cutting guide 105D in this manner.

The Resection Equipment 110 is provided with a variety of commands to perform bone or tissue operations. As with the Effector Platform 105, position information may be provided to the Resection Equipment 110 to specify where it should be located when performing resection. Other commands provided to the Resection Equipment 110 may be dependent on the type of resection equipment. For example, for a mechanical or ultrasonic resection tool, the commands may specify the speed and frequency of the tool. For Radiofrequency Ablation (RFA) and other laser ablation tools, the commands may specify intensity and pulse duration.

Some components of the CASS 100 do not need to be directly controlled by the Surgical Computer 150; rather, the Surgical Computer 150 only needs to activate the component, which then executes software locally specifying the manner in which to collect data and provide it to the Surgical Computer 150. In the example of FIG. 2A, there are two components that are operated in this manner: the Tracking System 115 and the Tissue Navigation System 120.

The Surgical Computer 150 provides the Display 125 with any visualization that is needed by the Surgeon 111 during surgery. For monitors, the Surgical Computer 150 may provide instructions for displaying images, GUIs, etc. using techniques known in the art. The display 125 can include various portions of the workflow of a surgical plan. During the registration process, for example, the display 125 can show a preoperatively constructed 3D bone model and depict the locations of the probe as the surgeon uses the probe to collect locations of anatomical landmarks on the patient. The display 125 can include information about the surgical target area. For example, in connection with a TKA, the display 125 can depict the mechanical and anatomical axes of the femur and tibia. The display 125 can depict varus and valgus angles for the knee joint based on a surgical plan, and the CASS 100 can depict how such angles will be affected if contemplated revisions to the surgical plan are made. Accordingly, the display 125 is an interactive interface that can dynamically update and display how changes to the surgical plan would impact the procedure and the final position and orientation of implants installed on bone.

As the workflow progresses to preparation of bone cuts or resections, the display 125 can depict the planned or recommended bone cuts before any cuts are performed. The surgeon 111 can manipulate the image display to provide different anatomical perspectives of the target area and can have the option to alter or revise the planned bone cuts based on intraoperative evaluation of the patient. The display 125 can depict how the chosen implants would be installed on the bone if the planned bone cuts are performed. If the surgeon 111 choses to change the previously planned bone cuts, the display 125 can depict how the revised bone cuts would change the position and orientation of the implant when installed on the bone.

The display 125 can provide the surgeon 111 with a variety of data and information about the patient, the planned surgical intervention, and the implants. Various patient-specific information can be displayed, including real-time data concerning the patient's health such as heart rate, blood pressure, etc. The display 125 also can include information about the anatomy of the surgical target region including the location of landmarks, the current state of the anatomy (e.g., whether any resections have been made, the depth and angles of planned and executed bone cuts), and future states of the anatomy as the surgical plan progresses. The display 125 also can provide or depict additional information about the surgical target region. For a TKA, the display 125 can provide information about the gaps (e.g., gap balancing) between the femur and tibia and how such gaps will change if the planned surgical plan is carried out. For a TKA, the display 125 can provide additional relevant information about the knee joint such as data about the joint's tension (e.g., ligament laxity) and information concerning rotation and alignment of the joint. The display 125 can depict how the planned implants' locations and positions will affect the patient as the knee joint is flexed. The display 125 can depict how the use of different implants or the use of different sizes of the same implant will affect the surgical plan and preview how such implants will be positioned on the bone. The CASS 100 can provide such information for each of the planned bone resections in a TKA or THA. In a TKA, the CASS 100 can provide robotic control for one or more of the planned bone resections. For example, the CASS 100 can provide robotic control only for the initial distal femur cut, and the surgeon 111 can manually perform other resections (anterior, posterior and chamfer cuts) using conventional means, such as a 4-in-1 cutting guide or jig 105D.

The display 125 can employ different colors to inform the surgeon of the status of the surgical plan. For example, un-resected bone can be displayed in a first color, resected bone can be displayed in a second color, and planned resections can be displayed in a third color. Implants can be superimposed onto the bone in the display 125, and implant colors can change or correspond to different types or sizes of implants.

The information and options depicted on the display 125 can vary depending on the type of surgical procedure being performed. Further, the surgeon 111 can request or select a particular surgical workflow display that matches or is consistent with his or her surgical plan preferences. For example, for a surgeon 111 who typically performs the tibial cuts before the femoral cuts in a TKA, the display 125 and associated workflow can be adapted to take this preference into account. The surgeon 111 also can preselect that certain steps be included or deleted from the standard surgical workflow display. For example, if a surgeon 111 uses resection measurements to finalize an implant plan but does not analyze ligament gap balancing when finalizing the implant plan, the surgical workflow display can be organized into modules, and the surgeon can select which modules to display and the order in which the modules are provided based on the surgeon's preferences or the circumstances of a particular surgery. Modules directed to ligament and gap balancing, for example, can include pre- and post-resection ligament/gap balancing, and the surgeon 111 can select which modules to include in their default surgical plan workflow depending on whether they perform such ligament and gap balancing before or after (or both) bone resections are performed.

For more specialized display equipment, such as AR HMDs, the Surgical Computer 150 may provide images, text, etc. using the data format supported by the equipment. For example, if the Display 125 is a holography device such as the Microsoft HoloLens™ or Magic Leap One™, the Surgical Computer 150 may use the HoloLens Application Program Interface (API) to send commands specifying the position and content of holograms displayed in the field of view of the Surgeon 111.

In some embodiments, one or more surgical planning models may be incorporated into the CASS 100 and used in the development of the surgical plans provided to the surgeon 111. The term "surgical planning model" refers to software that simulates the biomechanics performance of anatomy under various scenarios to determine the optimal way to perform cutting and other surgical activities. For example, for knee replacement surgeries, the surgical planning model can measure parameters for functional activities, such as deep knee bends, gait, etc., and select cut locations on the knee to optimize implant placement. One example of a surgical planning model is the LIFEMOD™ simulation software from SMITH AND NEPHEW, INC. In some embodiments, the Surgical Computer 150 includes computing architecture that allows full execution of the surgical planning model during surgery (e.g., a GPU-based parallel processing environment). In other embodiments, the Surgical Computer 150 may be connected over a network to a remote computer that allows such execution, such as a Surgical Data Server. As an alternative to full execution of the surgical planning model, in some embodiments, a set of transfer functions are derived that simplify the mathematical operations captured by the model into one or more predictor equations. Then, rather than execute the full simulation during surgery, the predictor equations are used. Further details on the use of transfer functions are described in WIPO Publication No. 2020/037308, filed Aug. 19, 2019, entitled "Patient Specific Surgical Method and System," the entirety of which is incorporated herein by reference.

FIG. 2B shows examples of some of the types of data that can be provided to the Surgical Computer 150 from the various components of the CASS 100. In some embodiments, the components may stream data to the Surgical Computer 150 in real-time or near real-time during surgery. In other embodiments, the components may queue data and send it to the Surgical Computer 150 at set intervals (e.g., every second). Data may be communicated using any format known in the art. Thus, in some embodiments, the components all transmit data to the Surgical Computer 150 in a common format. In other embodiments, each component may use a different data format, and the Surgical Computer

150 is configured with one or more software applications that enable translation of the data.

In general, the Surgical Computer 150 may serve as the central point where CASS data is collected. The exact content of the data will vary depending on the source. For example, each component of the Effector Platform 105 provides a measured position to the Surgical Computer 150. Thus, by comparing the measured position to a position originally specified by the Surgical Computer 150 (see FIG. 2B), the Surgical Computer can identify deviations that take place during surgery.

The Resection Equipment 110 can send various types of data to the Surgical Computer 150 depending on the type of equipment used. Example data types that may be sent include the measured torque, audio signatures, and measured displacement values. Similarly, the Tracking Technology 115 can provide different types of data depending on the tracking methodology employed. Example tracking data types include position values for tracked items (e.g., anatomy, tools, etc.), ultrasound images, and surface or landmark collection points or axes. The Tissue Navigation System 120 provides the Surgical Computer 150 with anatomic locations, shapes, etc. as the system operates.

Although the Display 125 generally is used for outputting data for presentation to the user, it may also provide data to the Surgical Computer 150. For example, for embodiments where a monitor is used as part of the Display 125, the Surgeon 111 may interact with a GUI to provide inputs which are sent to the Surgical Computer 150 for further processing. For AR applications, the measured position and displacement of the HMD may be sent to the Surgical Computer 150 so that it can update the presented view as needed.

One or more surgical parameters may be optimized with the CASS 100. For hip surgeries, the surgical parameters may comprise femoral neck resection location and angle, cup inclination angle, cup anteversion angle, cup depth, femoral stem design, femoral stem size, fit of the femoral stem within the canal, femoral offset, leg length, and femoral version of the implant.

Using the Point Probe to Acquire High-Resolution of Key Areas During Hip Surgeries Use of the point probe is described in U.S. patent application Ser. No. 14/955,742 entitled "Systems and Methods for Planning and Performing Image Free Implant Revision Surgery," the entirety of which is incorporated herein by reference. Briefly, an optically tracked point probe may be used to map the actual surface of the target bone that needs a new implant. Mapping is performed after removal of the defective or worn-out implant, as well as after removal of any diseased or otherwise unwanted bone. A plurality of points is collected on the bone surfaces by brushing or scraping the entirety of the remaining bone with the tip of the point probe. This is referred to as tracing or "painting" the bone. The collected points are used to create a three-dimensional model or surface map of the bone surfaces in the computerized planning system. The created 3D model of the remaining bone is then used as the basis for planning the procedure and necessary implant sizes. An alternative technique that uses X-rays to determine a 3D model is described in U.S. patent application Ser. No. 16/387,151, filed Apr. 17, 2019 and entitled "Three-Dimensional Selective Bone Matching" and U.S. patent application Ser. No. 16/789,930, filed Feb. 13, 2020 and entitled "Three-Dimensional Selective Bone Matching," the entirety of each of which is incorporated herein by reference.

For hip applications, the point probe painting can be used to acquire high resolution data in key areas such as the acetabular rim and acetabular fossa. This can allow a surgeon to obtain a detailed view before beginning to ream. For example, in one embodiment, the point probe may be used to identify the floor (fossa) of the acetabulum. As is well understood in the art, in hip surgeries, it is important to ensure that the floor of the acetabulum is not compromised during reaming so as to avoid destruction of the medial wall. If the medial wall were inadvertently destroyed, the surgery would require the additional step of bone grafting. With this in mind, the information from the point probe can be used to provide operating guidelines to the acetabular reamer during surgical procedures. For example, the acetabular reamer may be configured to provide haptic feedback to the surgeon when he or she reaches the floor or otherwise deviates from the surgical plan. Alternatively, the CASS 100 may automatically stop the reamer when the floor is reached or when the reamer is within a threshold distance.

As an additional safeguard, the thickness of the area between the acetabulum and the medial wall could be estimated. For example, once the acetabular rim and acetabular fossa has been painted and registered to the pre-operative 3D model, the thickness can readily be estimated by comparing the location of the surface of the acetabulum to the location of the medial wall. Using this knowledge, the CASS 100 may provide alerts or other responses in the event that any surgical activity is predicted to protrude through the acetabular wall while reaming.

The point probe may also be used to collect high resolution data of common reference points used in orienting the 3D model to the patient. For example, for pelvic plane landmarks like the ASIS and the pubic symphysis, the surgeon may use the point probe to paint the bone to represent a true pelvic plane. Given a more complete view of these landmarks, the registration software has more information to orient the 3D model.

The point probe may also be used to collect high-resolution data describing the proximal femoral reference point that could be used to increase the accuracy of implant placement. For example, the relationship between the tip of the Greater Trochanter (GT) and the center of the femoral head is commonly used as reference point to align the femoral component during hip arthroplasty. The alignment is highly dependent on proper location of the GT; thus, in some embodiments, the point probe is used to paint the GT to provide a high-resolution view of the area. Similarly, in some embodiments, it may be useful to have a high-resolution view of the Lesser Trochanter (LT). For example, during hip arthroplasty, the Dorr Classification helps to select a stem that will maximize the ability of achieving a press-fit during surgery to prevent micromotion of femoral components post-surgery and ensure optimal bony ingrowth. As is generated understood in the art, the Dorr Classification measures the ratio between the canal width at the LT and the canal width 10 cm below the LT. The accuracy of the classification is highly dependent on the correct location of the relevant anatomy. Thus, it may be advantageous to paint the LT to provide a high-resolution view of the area.

In some embodiments, the point probe is used to paint the femoral neck to provide high-resolution data that allows the surgeon to better understand where to make the neck cut. The navigation system can then guide the surgeon as they perform the neck cut. For example, as understood in the art, the femoral neck angle is measured by placing one line down the center of the femoral shaft and a second line down the center of the femoral neck. Thus, a high-resolution view of the femoral neck (and possibly the femoral shaft as well) would provide a more accurate calculation of the femoral neck angle.

High-resolution femoral head neck data also could be used for a navigated resurfacing procedure where the software/hardware aids the surgeon in preparing the proximal femur and placing the femoral component. As is generally understood in the art, during hip resurfacing, the femoral head and neck are not removed; rather, the head is trimmed and capped with a smooth metal covering. In this case, it would be advantageous for the surgeon to paint the femoral head and cap so that an accurate assessment of their respective geometries can be understood and used to guide trimming and placement of the femoral component.

Registration of Pre-Operative Data to Patient Anatomy Using the Point Probe

As noted above, in some embodiments, a 3D model is developed during the pre-operative stage based on 2D or 3D images of the anatomical area of interest. In such embodiments, registration between the 3D model and the surgical site is performed prior to the surgical procedure. The registered 3D model may be used to track and measure the patient's anatomy and surgical tools intraoperatively.

During the surgical procedure, landmarks are acquired to facilitate registration of this pre-operative 3D model to the patient's anatomy. For knee procedures, these points could comprise the femoral head center, distal femoral axis point, medial and lateral epicondyles, medial and lateral malleolus, proximal tibial mechanical axis point, and tibial A/P direction. For hip procedures these points could comprise the anterior superior iliac spine (ASIS), the pubic symphysis, points along the acetabular rim and within the hemisphere, the greater trochanter (GT), and the lesser trochanter (LT).

In a revision surgery, the surgeon may paint certain areas that contain anatomical defects to allow for better visualization and navigation of implant insertion. These defects can be identified based on analysis of the pre-operative images. For example, in one embodiment, each pre-operative image is compared to a library of images showing "healthy" anatomy (i.e., without defects). Any significant deviations between the patient's images and the healthy images can be flagged as a potential defect. Then, during surgery, the surgeon can be warned of the possible defect via a visual alert on the display 125 of the CASS 100. The surgeon can then paint the area to provide further detail regarding the potential defect to the Surgical Computer 150.

In some embodiments, the surgeon may use a non-contact method for registration of bony anatomy intra-incision. For example, in one embodiment, laser scanning is employed for registration. A laser stripe is projected over the anatomical area of interest and the height variations of the area are detected as changes in the line. Other non-contact optical methods, such as white light interferometry or ultrasound, may alternatively be used for surface height measurement or to register the anatomy. For example, ultrasound technology may be beneficial where there is soft tissue between the registration point and the bone being registered (e.g., ASIS, pubic symphysis in hip surgeries), thereby providing for a more accurate definition of anatomic planes.

Navigated Reaming of the Acetabulum

As discussed herein, imagery of the acetabulum may be collected either pre-operatively or intraoperatively using MRI, CT, X-ray, ultrasound, or any other modality known in the art. Alternatively, a point probe may be used to map the actual surface of the acetabulum. The data collected from one or a combination of the above techniques may be used to generate a three-dimensional model of at least a portion of the acetabulum.

Figure 3:
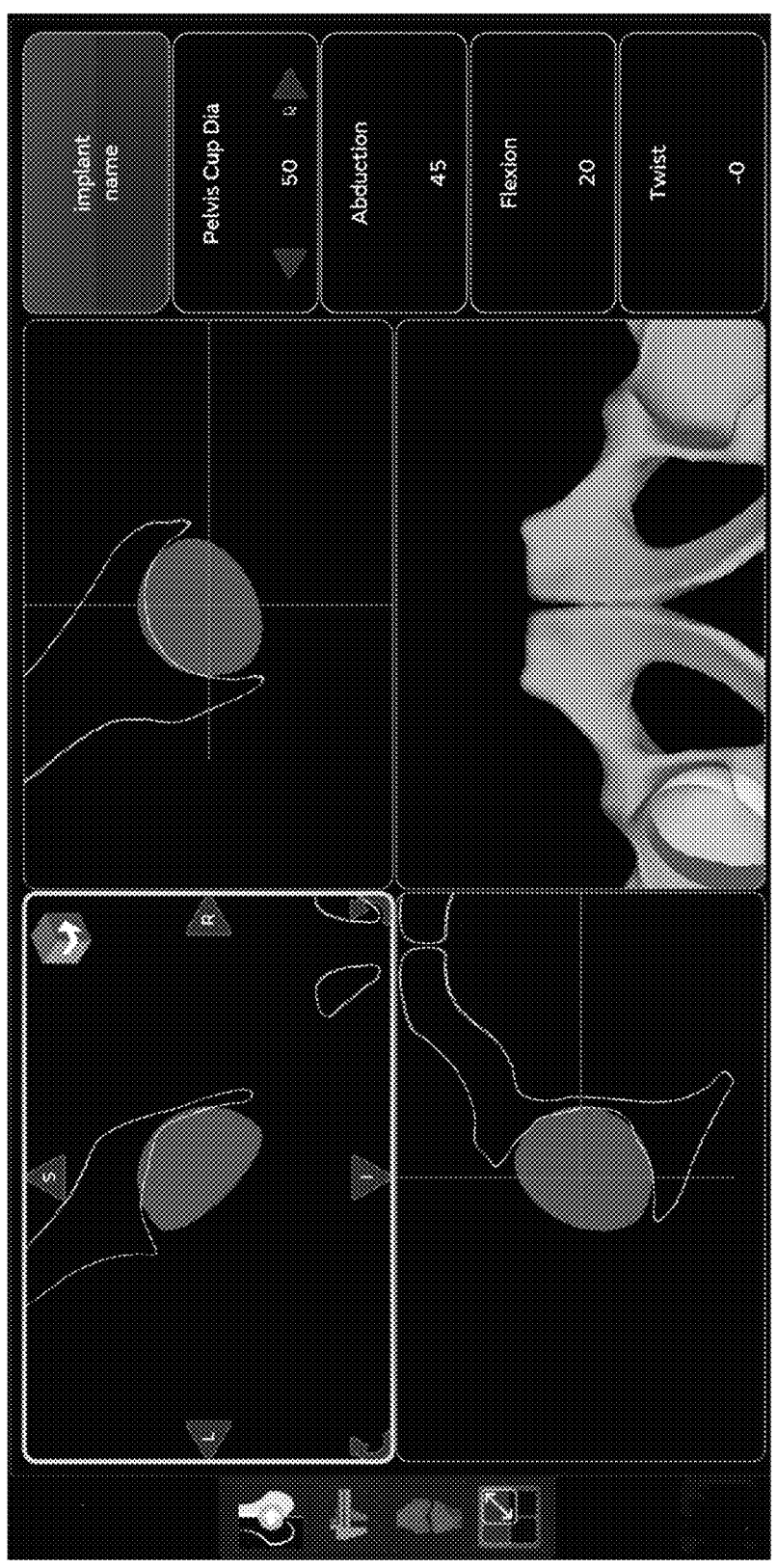
FIG. 3 depicts illustrative graphical user interfaces including images depicting an implant placement in accordance with an embodiment.

FIG. 3 depicts an illustrative graphical user interface 300 for configuring implant placement for a THA in accordance with an embodiment. The graphical user interface 300 may depict the implant interfaced to the three-dimensional model of the acetabulum from one or more views. The views may include planar views or three-dimensional views. One or more of the views may be interactive, allowing the surgeon to move the implant with respect to the acetabulum. The graphical user interface 300 may depict variables associated with the implant (e.g., cup diameter) and the hip (e.g., abduction, flexion, and twist). The system may provide an optimal placement and/or sizing of the implant. The implant placement may comprise a location and an orientation of the implant. Variables associated with the implant may be configurable by the surgeon. Variables associated with the hip may be given suggested values by the surgeon, which the system may use in providing an optimized implant position and/or sizing. The information generated by the system and/or the surgeon in interface with the graphical user interface 300 may be compiled into a surgical plan. The surgical plan may include a modified version of the three-dimensional model that includes the planned resections to the bone.

Figure 4:
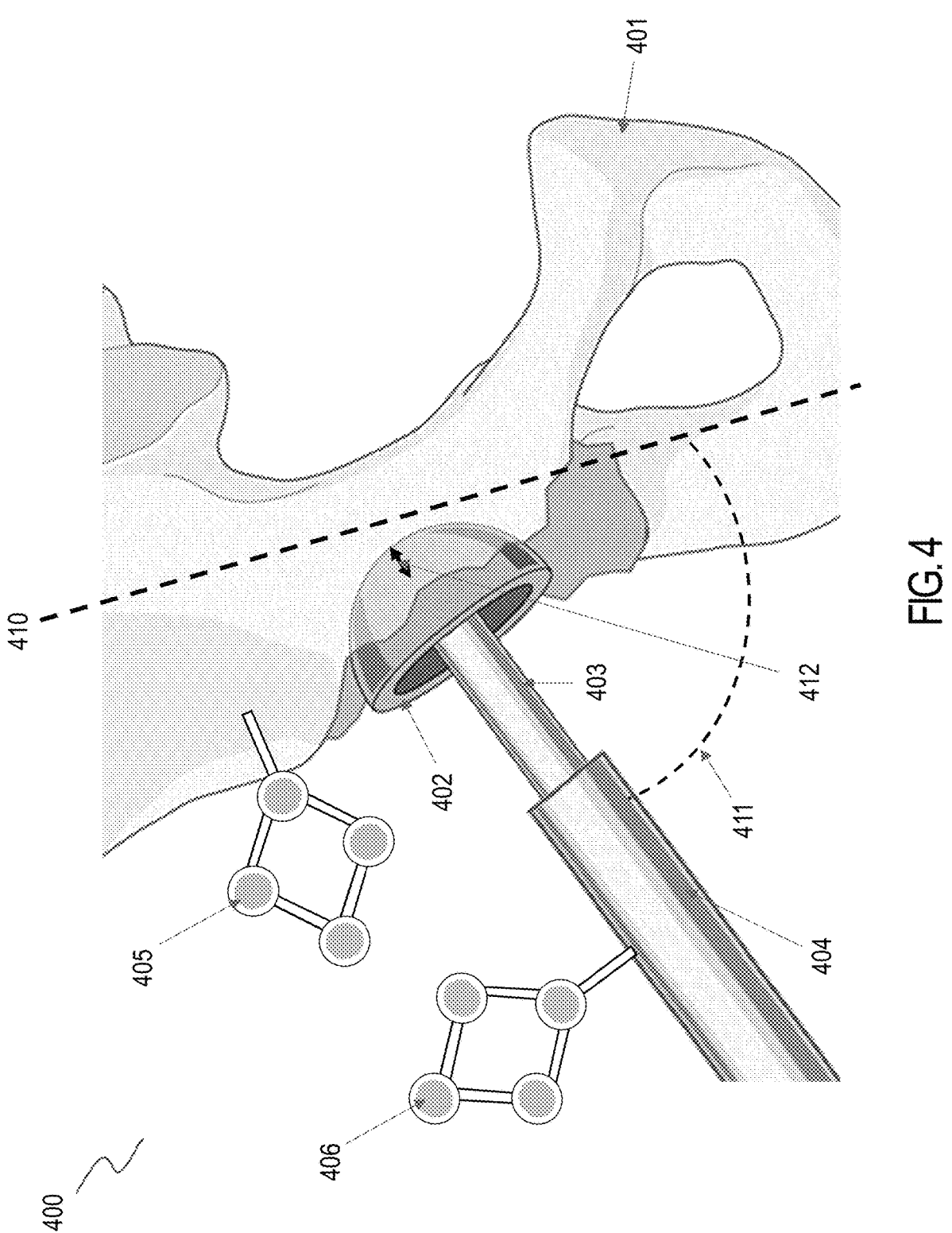
FIG. 4 depicts an environment for navigated acetabular reaming in accordance with an embodiment.

FIG. 4 depicts an environment 400 for navigated acetabular reaming in accordance with an embodiment. The reamer may comprise a shaft 403 configured to drive the reamer head 402. The shaft 403 may be interfaced to a surgical drill (not shown). In some embodiments, the reamer may further comprise an outer casing 404 for the shaft 403. The outer casing 404 may be configured to remain stationary when the shaft 403 is spinning. The surgical drill may be manually operated by the surgeon. The surgical drill may be interfaced to a robotic and/or passive arm. As an example, the robotic and/or passive arm may partially restrict the manual movement of the surgical drill along a predetermined plane, line, or zone, with respect to the acetabulum 401, as defined in the surgical plan and based on the position of the reamer head 402 as determined using the methods herein.

Within the environment 400, at least two tracking elements may be provided, with at least one tracking element 405 affixed to the patient's anatomy at or near the acetabulum 401, and at least one tracking element 406 affixed the reamer. The tracking element 406 affixed to the reamer may be attached to any non-rotating portion of the reamer such as the base, handle, outer casing 404, and/or robotic/passive arm, so long as the spatial relationship to the reamer head 402 is known. Preferably, the elements 406 are positioned and oriented so as not to cause interference in performing the reaming, i.e., to avoid contacting one another, the patient anatomy, the surgical drill, the reamer, and/or other objects within the surgical environment. Though optical trackers are depicted, any tracking method (e.g., EM, optical codes, fiber optic) or a combination thereof, may be employed.

The reamer may be in communication to the CASS 100 through any known means including wired (e.g., Universal Serial Bus) and wireless (e.g., 802.11 or Bluetooth®) communication systems.

The CASS 100 may also receive information relating to the geometry of the reamer including the location of the tracking element 406 in relation to the distal end of the reamer head 402. The information may further include the size of the reamer head 402. Portions of the information may be specified in the surgical plan and/or provided intraoperatively. Portions of the information may be manually entered, through a user interface, or collected by other techniques. As an example, the CASS 100 may scan an element (e.g., a barcode, QR code, or RFID chip) associated with the reamer which may either encode the information or reference the system to a database entry storing the information. In another example, the CASS 100 may identify the reamer through image recognition techniques and look up the information in a database.

During a procedure, the CASS 100 may determine a depth 412 of the reamer with respect to the acetabulum 401, based on the respective locations of the tracking elements 405/406, the three-dimensional model of the acetabulum 401, and the geometric information relating to the reamer. The depth 412 may measure the distance the distal end of the reamer head 402 has reamed into the acetabulum 401. The depth 412 may be measured along the axis of shaft 403 of the reamer.

During the procedure, the CASS 100 may determine a tilt angle 411 of the reamer. The tilt angle 411 may be determined with respect to any plane 410, based on the respective locations of the tracking elements 405/406, the three-dimensional model of the acetabulum 401, and the geometric information relating to the reamer. The plane may be predetermined by the surgeon as part of the surgical plan or selected by the CASS 100. In some embodiments, the plane 410 may translate based on the depth 412. As example, the plane 410 may be the anterior-posterior plane. In another example, the plane 410 may be a plane parallel to the anterior-posterior plane defined by the plane's adjacency to the distal point of the reamer head 402. In a third example, the plane 410 may be a randomly preselected plane intersecting and/or near the acetabulum 401. Determining the tilt angle 411 may include projecting the axis of the shaft 403 of the reamer onto the plane 410 and calculating the angle between the axis of the shaft 403 and the projected line.

Figure 5:
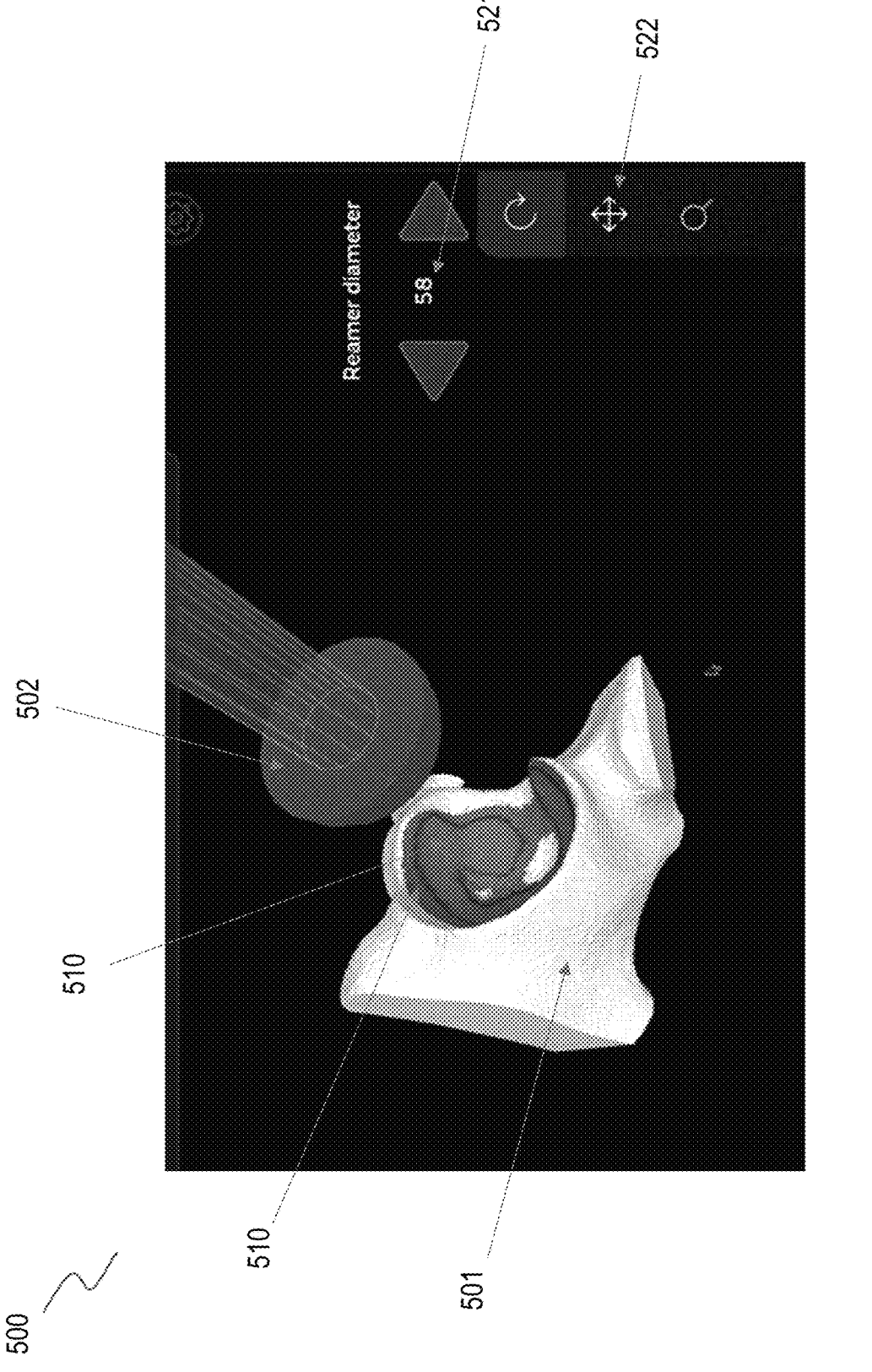
FIG. 5 depicts an illustrative graphical user interface for navigated acetabular reaming in accordance with an embodiment.

Based on the depth 412 and tilt angle 411 of the reamer with respect to the acetabulum 401, the CASS 100 may determine the volume of removed bone from the three-dimensional model. FIG. 5 depicts an illustrative graphical user interface 500 for navigated acetabular reaming in accordance with an embodiment. The graphical user interface 500 may depict a portion of the three-dimensional model of the acetabulum 501. The graphical user interface 500 may depict the position of the reamer head 502 relative to the three-dimensional model 501.

Regions 510 of the three-dimensional mode 501 may be coded based on the volume of bone removal necessary at a location, based on the surgical plan. The coding may be based on colors, symbols, and/or patterns. As an example, a region 510 may be green when the region 510 requires a relatively large amount of reaming to reach the target depth for the region based on the surgical plan. The region may vary in color through a spectrum of yellow, orange, and red as the region approaches the target depth. In another example, regions 510 may be striped, with the density of stripes correlating to the change in depth required to reach the target depth in the surgical plan. A person of ordinary skill in the art will recognize that any color, symbol, or pattern may be used to designate the remaining volume requiring reaming on the three-dimensional model 501. Additional information may also be encoded into each region. As an example, a color, symbol, and/or pattern may visually depict the estimated bone density of a region.

Thresholds between varying coding color, symbols, and/or patterns may be based on predetermined distances between the surface of the three-dimensional model and the planned modifications in the surgical plan. Responsive to changes in thresholds and/or contact between the bone and reamer, the CASS 100 may alert the surgeon. An alert may be audio, visual, and/or haptic.

Based on the determined depth of the reamer, the tilt angle of the reamer, and the geometry of the reamer, the reamer head 502 may be continuously tracked with respect to the acetabulum. The CASS 100 may operate under the assumption that when the estimated volume occupied by the reamer head 502 overlaps the volume of the three-dimensional model 501 that the overlapping volume of bone has been removed in the patient. The three-dimensional model 501 may be modified based on an estimated overlap of the reamer head 502 and the three-dimensional model 501. The modification may include removing the volume of the model 501 within the overlap.

The graphical user interface 500 may feature one or more interface elements. Example elements may include a manual input from the reamer diameter and one or more inputs 522 for manipulating the viewpoint (i.e., viewing angle, pan, and zoom) of the three-dimensional model 501. A person of ordinary skill in the art will note that due to the low processing requirements of the methods for locating the reamer with respect to the acetabulum, the display may depict the real-time status (i.e., volume) and relative locations of the acetabulum and the reamer.

Figure 6:
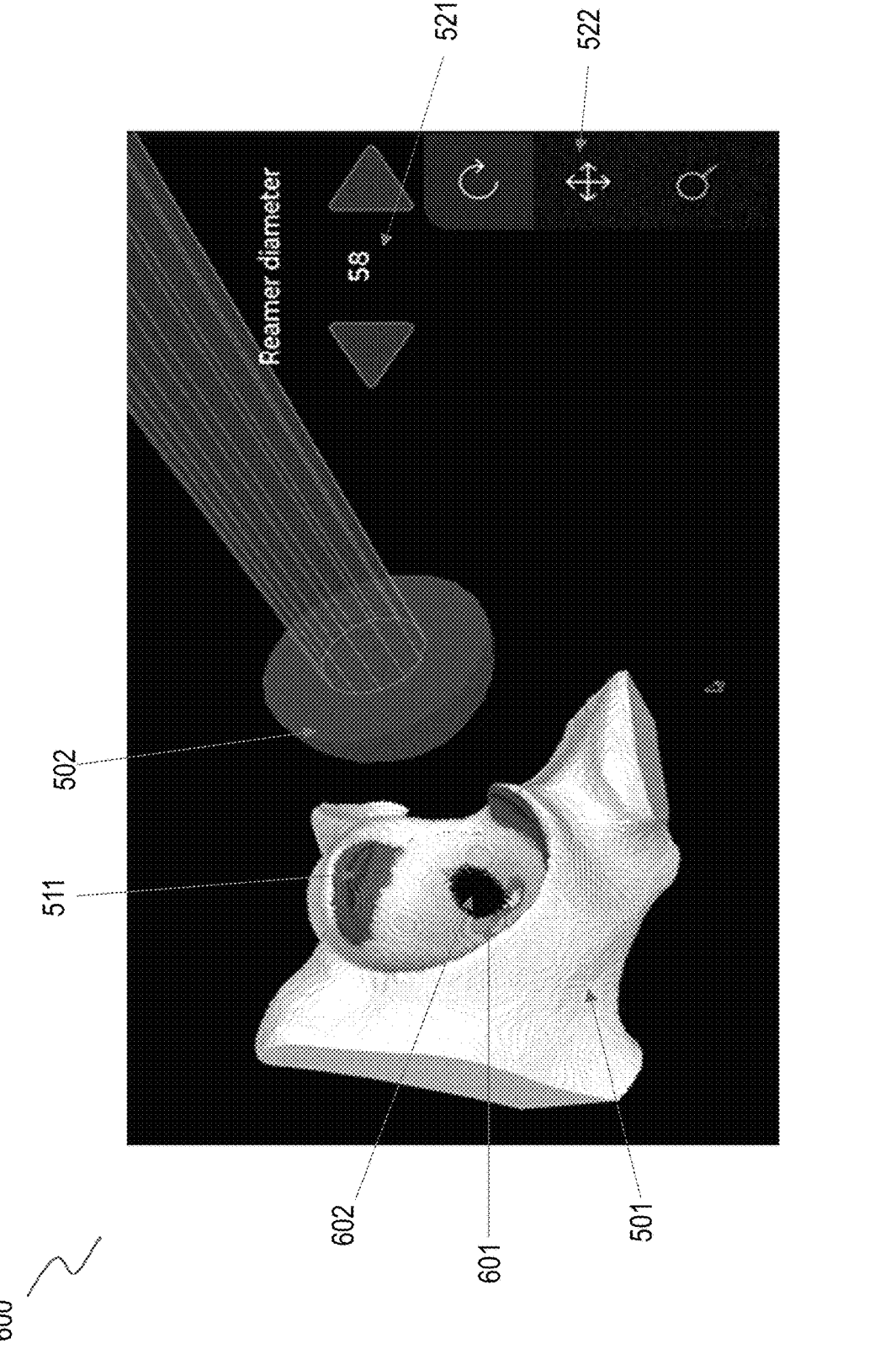
FIG. 6 depicts an illustrative graphical user interface for navigated acetabular reaming in accordance with an embodiment.

FIG. 6 depicts an illustrative graphical user interface for navigated acetabular reaming in accordance with an embodiment. The graphical user interface 600 may depict a portion of the three-dimensional model of the acetabulum 501. The graphical user interface 600 may depict the position of the reamer head 502 relative to the three-dimensional model 501.

Regions of the three-dimensional mode 501 may be coded based on the volume of bone removal necessary at a location, based on the surgical plan. The coding may be based on colors, symbols, and/or patterns as described above in reference to FIG. 5. The three-dimensional model 501 may be modified based on an estimated overlap of the reamer head 502 and the three-dimensional model 501. The modification may include removing the volume of the model 501 within the overlap.

As a region approaches the depth specified in the surgical plane, the region 601 may be coded to identify that the region requires no additional bone removal. As an example, the region 601 may be colored red. A distinct coding may exist to alert the surgeon that a region 602 is at and/or beyond the threshold depth specified within the surgical plan. As an example, the region 602 may be colored black. In the scenario that the reamer head 502 is in contact with a region 602 at and/or beyond the threshold depth, the reamer may be automatically deactivated, reduced in speed, and/or restricted in movement. For example, the CASS 100 may deactivate the surgical drill and/or reamer 502 to prevent further reaming at such a region 602. In some embodiments, responsive to a region approaching, reaching, and/or surpassing the threshold depth, the CASS 100 may provide an alert to the surgeon. An alert may be audio, visual, and/or haptic.

In certain embodiments, the three-dimensional model may be an atlas model selected from a database. The atlas model may be chosen based on a comparison of one or more features of the patient's anatomy. The atlas model may be chosen using a machine learning algorithm. That atlas model may be transformed to more accurately match the patient anatomy based on data collected through standard imaging, MRI, CT, X-ray, ultrasound, point probe, and or manual entry. As an example, based on detected landmarks in an X-ray, an atlas model similar to the patient's anatomy may be chosen. The model may then be scaled to match the patient's dimensions. The scaled model may be used for determining implant placement. The scaled model may then be further modified intraoperatively using a point probe so that the bone requiring reaming is accurately modeled.

In certain embodiments, a three-dimensional model of the acetabulum may not be available. The tracking elements 405 affixed to the patient anatomy may be registered to a planned implant placement. The volume of bone requiring resection above the planned implant placement may be captured intraoperatively (i.e., with imaging and/or a point probe).

During the procedure, the CASS 100 may determine a depth 412 of the reamer with respect to the planned implant position, based on the respective locations of the tracking elements 405/406, and the geometric information relating to the reamer. The depth 412 may measure the distance between the distal end of the reamer head 402 and the surface of the planned implant position. The depth 412 may be measured along the axis of shaft 403 of the reamer.

During the procedure, the CASS 100 may determine a tilt angle 411 of the reamer. The tilt angle 411 may be determined with respect to any plane 410, based on the respective locations of the tracking elements 405/406, the planned implant position, and the geometric information relating to the reamer. The plane may be predetermined by the surgeon as part of the surgical plan or selected by the CASS 100. In some embodiments, the plane 410 may translate based on the depth 412. As example, the plane 410 may be the anterior-posterior plane. In another example, the plane 410 may be a plane parallel to the anterior-posterior plane defined by the plane's adjacency to the distal point of the reamer head 402. In a third example, the plane 410 may be a randomly preselected plane intersecting and/or near the acetabulum 401. Determining the tilt angle 411 may include projecting the axis of the shaft 403 of the reamer onto the plane 410 and calculating the angle between the axis of the shaft 403 and the projected line.

In certain embodiments, the CASS 100 may not have information associated with the volume of bone above planned implant placement. In further embodiments, the CASS 100 may determine the location of bone based on a torque applied to the reamer when interacting with the bone. As an example, prior to contact the bone with the reamer, a display may depict the location of the reamer head with respect to the planned implant position. After detecting a torque on the reamer, the display may be updated to reflect similar information as described in reference to FIGS. 5 and 6.

In other embodiments, the display may depict a color, symbol, and/or pattern on a region of the planned implant placement responsive to the reamer head reaching and/or at a threshold near the planned implant placement.

Figure 7:
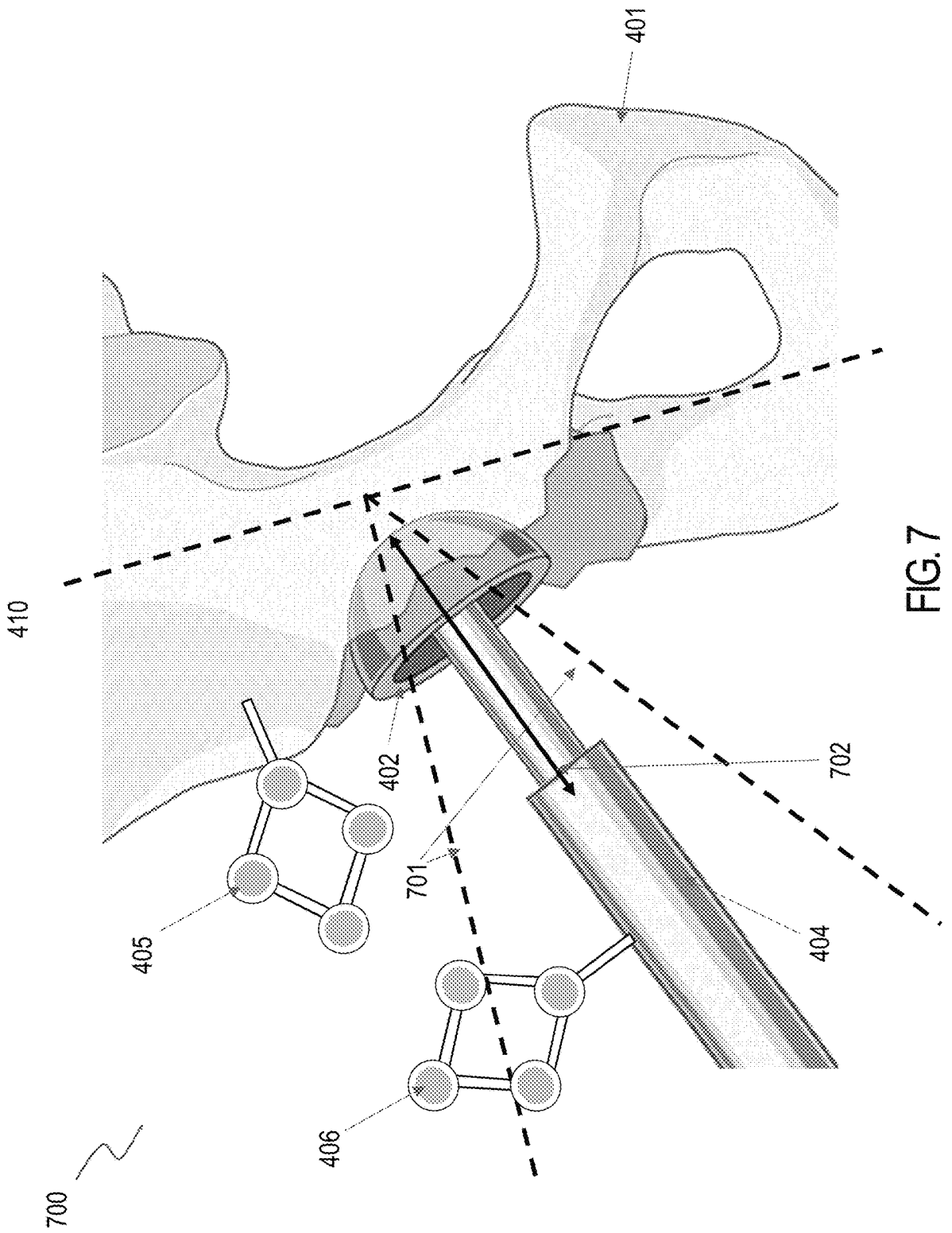
FIG. 7 depicts an illustrative environment with boundaries for the control of a reamer during navigated acetabular reaming in accordance with an embodiment.

FIG. 7 depicts an illustrative environment 700 with boundaries for the control of a reamer during navigated acetabular reaming in accordance with an embodiment. One or more boundaries may be established to manage control of the reamer. Responsive to the surgeon reaching a boundary, the CASS 100 may deactivate and/or activate the reamer, reduce the rotational speed of the reamer, limit the movement of the reamer, and/or alert the surgeon. An alert may be audio, visual, and/or haptic. Boundaries of any form (e.g., spheres, hemispheres, cubes, etc.) may be established in a surgical plan. Based on the methods for locating the reamer head 402 with respect to the acetabulum 401, as described herein, a cone may be a boundary established with minimal processing requirements. The cone may be defined based on a pair of angles 701 from the reference plane 410, and a maximum depth away 702 from the surface of the acetabulum 401. Proper definition of boundaries may aid in determining when bone is being removed as opposed to when the reamer is being adjusted or repositioned. A person of ordinary skill in the art will note that a boundary may include an open-ended shape and/or a combination of shapes. For example, a cone may be defined with an angle, but no maximum depth.

Figure 8B:
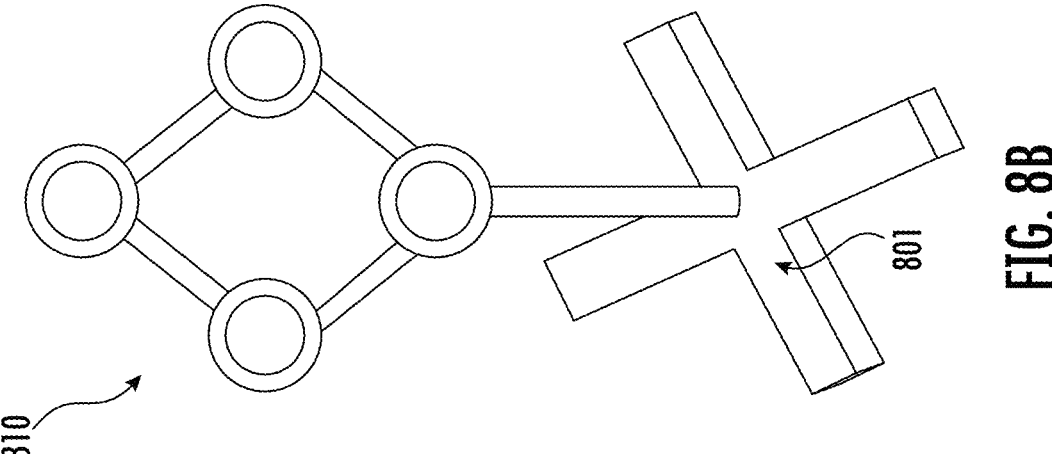
FIG. 8B depicts an illustrative tracking element configured to replace a reamer head for calibration in accordance with an embodiment.
Figure 8A:
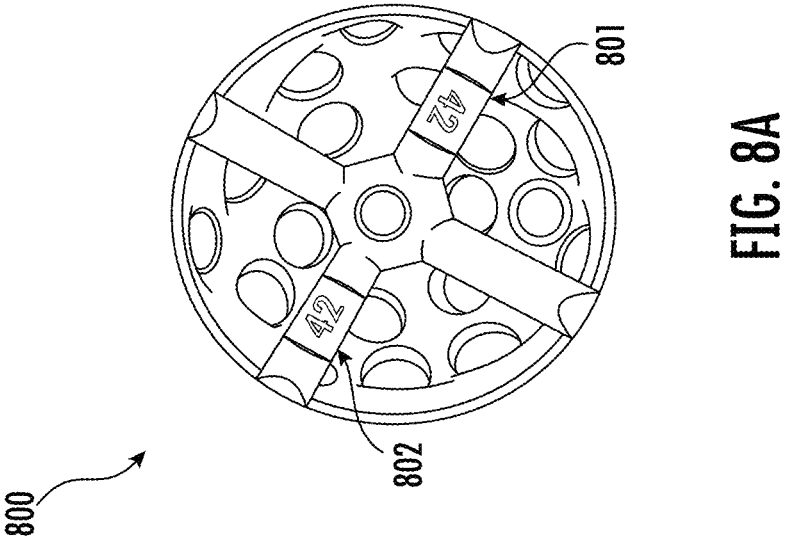
FIG. 8A depicts an illustrative reamer head in accordance with an embodiment.

FIG. 8A depicts an illustrative reamer head 800 in accordance with an embodiment. The diameter of the reamer head 800 may be identified by any of the methods described herein. Alternatively, the CASS 100 may read a label 802 providing information associated with the diameter of the reamer head 800 using imaging and optical character recognition (OCR).

The reamer head 800 may feature an interface element 801 configured to facilitate connecting the reamer head 800 to the shaft 403 of the drill. For example, many reamer heads 800 feature a cross shaped interface. FIG. 8B depicts an illustrative tracking element 810 configured to replace a reamer head 800 for calibration in accordance with an embodiment. The tracking element 810 may include a similar interface element 801 as featured on the reamer head 800. Prior to attaching the reamer head 800, the tracking element 810 may be interfaced to the reamer shaft 403. The location of the end of the shaft 403 may be determined by registering the location of the tracking element 810 with another tracking element affixed to the reamer, e.g., tracking element 406 affixed to the outer casing 404 or elsewhere on the reamer. Though optical trackers are depicted, any tracking method (e.g., EM, optical codes, fiber optic) or a combination thereof, may be employed.

Although the systems and methods, as described herein, refer to the hip, a person of ordinary skill in the art will understand that similar systems and methods may be applied to other joints such as the shoulder.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure that are within known or customary practice in the art to which these teachings pertain.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, devices, or systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 components refers to groups having 1, 2, or 3 components. Similarly, a group having 1-5 components refers to groups having 1, 2, 3, 4, or 5 components, and so forth.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $\frac{1}{10}$ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values, e.g., variations in the numerical quantity of such values that can occur, but would be recognized to be equivalents by a person skilled in the art.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A system for performing navigated reaming of an acetabulum, the system comprising:
    a navigational tracking system;
    a reamer;
    a first tracking element affixed to the reamer and configured to be tracked by the navigational tracking system;
    a second tracking element affixed to an acetabulum and configured to be tracked by the navigational tracking system; and
a processor in communication with the navigational tracking system, the processor programmed to:
    receive a surgical plan, wherein the surgical plan comprises one or more patient-specific parameters associated with a total hip arthroplasty, wherein the one or more patient-specific parameters comprise a planned implant location and orientation,
    receive a three-dimensional model of at least a portion of the acetabulum,
    determine at least one of a depth and a tilt angle of the reamer with respect to the acetabulum and the planned implant location and orientation based on a location of the first tracking element, a location of the second tracking element, and information associated with a geometry of the reamer, and
    modify the three-dimensional model based on at least one of the depth and the tilt angle to generate an updated three-dimensional model of at least a portion of the acetabulum,
    compare the updated three-dimensional model of at least a portion of the acetabulum and the three-dimensional model of the acetabulum, and
    display indicia on the updated three-dimensional model of at least a portion of the acetabulum based on the comparison.

2. The system of claim 1, wherein the processor is further programmed to:
    compare the tilt angle with a threshold range of angles; and
    responsive to the tilt angle lying outside the threshold range of angle, automatically deactivate or reduce a speed of the reamer.

3. The system of claim 1, wherein the processor is further programmed to:
    compare the depth with a threshold depth; and
    responsive to the depth exceeding the threshold depth, automatically deactivate or reduce a speed of the reamer.

4. The system of claim 1, wherein the processor is further programmed to:
    receive a size of a reamer head, and
    determine a location of the reamer head based on the size of the reamer head and the location of the first tracking element.

5. The system of claim 4, further comprising a display device; and
wherein the processor is further programmed to:
    generate a three-dimensional model of the reamer head, and
    display, on the display device, the three-dimensional model of the reamer head relative to the three-dimensional model of at least a portion of the acetabulum.

6. The system of claim 1, further comprising:
    a third tracking element configured to interface to the reamer in place of a reamer head; and
    wherein the processor is further configured to determine the information associated with the geometry of the reamer based on the location of the first tracking element with respect to a location of the third tracking element.

* * * * *